US012447353B2

(12) United States Patent
Johnson et al.

(10) Patent No.: US 12,447,353 B2
(45) **Date of Patent: *Oct. 21, 2025**

(54) LIGHT THERAPY DEVICE AND METHOD FOR DELIVERY OF LIGHT THERAPY TO A BODY PART

(71) Applicant: BioPhotas, Inc., Anaheim, CA (US)

(72) Inventors: Patrick Lamberth Johnson, Tustin, CA (US); Kathleen Stanton Buchanan, Laguna Beach, CA (US)

(73) Assignee: BioPhotas, Inc., Tustin, CA (US)

( * ) Notice: Subject to any disclaimer, the term of this patent is extended or adjusted under 35 U.S.C. 154(b) by 1257 days.

This patent is subject to a terminal disclaimer.

(21) Appl. No.: 17/162,966

(22) Filed: Jan. 29, 2021

(65) Prior Publication Data

US 2021/0252301 A1 Aug. 19, 2021

Related U.S. Application Data

(63) Continuation of application No. 15/980,277, filed on May 15, 2018, now abandoned, which is a (Continued)

(51) Int. Cl.
*A61N 5/06* (2006.01)

(52) U.S. Cl.
CPC ............ *A61N 5/06* (2013.01); *A61N 5/0613* (2013.01); *A61N 5/0616* (2013.01); (Continued)

(58) Field of Classification Search
CPC ...... A61N 5/06; A61N 5/0613; A61N 5/0616; A61N 5/0601; A61N 2005/0626; (Continued)

(56) References Cited

U.S. PATENT DOCUMENTS

| | | | |
|---|---|---|---|
| 5,000,752 | A | 3/1991 | Hoskin et al. |
| D337,642 | S | 7/1993 | Yamasaki et al. |

(Continued)

FOREIGN PATENT DOCUMENTS

| | | |
|---|---|---|
| WO | WO 2011/001344 A2 | 1/2011 |

OTHER PUBLICATIONS

Definition of Plastic Deformation. Collins Dictionary, retrieved on Jan. 3, 2024, Retrieved from the Internet: <https://www.collinsdictionary.com/us/dictionary/english/plastic-deformation> (Year: 2024).*

(Continued)

*Primary Examiner* — Niketa Patel
*Assistant Examiner* — Sebastian X Lukjan
(74) *Attorney, Agent, or Firm* — Robert D. Buyan; Stout, Uxa & Buyan, LLP

(57) ABSTRACT

Methods, devices and systems for delivering light therapy to human or non-human animal subjects. Included are shapeable light therapy devices which are formable into different shapes suitable for delivery of therapeutic light to different regions of the subject's body and will retain the desired shape without a need for the use of a strap or other shape-retaining apparatus. Also included are light therapy devices that, in at least some modes of operation, deliver light that is not visible to the human eye and which include indicator(s) to indicate to a user and/or to the subject being treated when non-visible light is actually being emitted.

21 Claims, 52 Drawing Sheets

Related U.S. Application Data continuation of application No. 14/534,083, filed on Nov. 5, 2014, now Pat. No. 9,968,799, which is a continuation of application No. 13/672,554, filed on Nov. 8, 2012, now Pat. No. 8,900,283.

(60) Provisional application No. 61/557,319, filed on Nov. 8, 2011.

(52) U.S. Cl.
CPC .... *A61N 5/0601* (2013.01); *A61N 2005/0626* (2013.01); *A61N 2005/0632* (2013.01); *A61N 2005/0642* (2013.01); *A61N 2005/0643* (2013.01); *A61N 2005/0645* (2013.01); *A61N 2005/0652* (2013.01); *A61N 2005/0659* (2013.01); *A61N 2005/0663* (2013.01)

(58) Field of Classification Search
CPC .... A61N 2005/0632; A61N 2005/0642; A61N 2005/0643; A61N 2005/0645; A61N 2005/0652; A61N 2005/0659; A61N 2005/0663
See application file for complete search history.

(56) References Cited

U.S. PATENT DOCUMENTS

| | | | | |
|---|---|---|---|---|
| 6,221,095 | B1 | 4/2001 | Zuylen et al. | |
| 6,596,016 | B1 | 7/2003 | Vreman et al. | |
| 6,743,249 | B1 | 6/2004 | Alden et al. | |
| D497,882 | S | 11/2004 | Huang | |
| D579,572 | S | 10/2008 | Wittenbrock et al. | |
| D623,308 | S | 9/2010 | Kramer | |
| D664,932 | S | 8/2012 | Sedic | |
| D684,269 | S | 6/2013 | Wang et al. | |
| 8,756,731 | B1 | 6/2014 | Huttner et al. | |
| 8,900,283 | B2 * | 12/2014 | Johnson | A61N 5/0616 607/90 |
| D732,677 | S | 6/2015 | Kristensen et al. | |
| D802,779 | S | 11/2017 | Inoue et al. | |
| 9,968,799 | B2 * | 5/2018 | Johnson | A61N 5/0613 |
| D858,463 | S | 9/2019 | Nien et al. | |
| D870,909 | S | 12/2019 | Sedic | |
| D879,053 | S | 3/2020 | Yu | |
| D879,341 | S | 3/2020 | Kassin et al. | |
| D890,752 | S | 7/2020 | Huang et al. | |
| D894,368 | S | 8/2020 | Lee | |
| D925,046 | S | 7/2021 | Johnson | |
| 2002/0143373 | A1 | 10/2002 | Courtnage et al. | |
| 2003/0009205 | A1 | 1/2003 | Biel | |
| 2004/0138726 | A1 | 7/2004 | Savage et al. | |
| 2005/0110702 | A1 | 5/2005 | Aoki et al. | |
| 2006/0217690 | A1 | 9/2006 | Bastin et al. | |
| 2007/0129776 | A1 | 6/2007 | Robins et al. | |
| 2007/0156208 | A1 * | 7/2007 | Havell | A61N 5/0616 607/88 |
| 2007/0167999 | A1 | 7/2007 | Breden et al. | |
| 2007/0208395 | A1 * | 9/2007 | Leclerc | A61N 5/0616 607/86 |
| 2007/0208396 | A1 | 9/2007 | Whatcott et al. | |
| 2007/0217199 | A1 | 9/2007 | Adam et al. | |
| 2007/0283655 | A1 * | 12/2007 | Tobin | A61N 5/0616 52/478 |
| 2009/0105791 | A1 | 4/2009 | McGinnis et al. | |
| 2010/0114007 | A1 | 5/2010 | Fischer et al. | |
| 2010/0234927 | A1 | 9/2010 | Lin | |
| 2010/0274329 | A1 | 10/2010 | Bradley et al. | |
| 2010/0318161 | A1 | 12/2010 | Brawn | |
| 2011/0077675 | A1 | 3/2011 | Rofougaran | |
| 2011/0144724 | A1 | 6/2011 | Pryor et al. | |
| 2011/0144727 | A1 | 6/2011 | Benedict | |
| 2012/0253433 | A1 | 10/2012 | Rosen et al. | |
| 2013/0274839 | A1 | 10/2013 | Johnson et al. | |
| 2014/0128941 | A1 | 5/2014 | Williams | |
| 2014/0128942 | A1 | 5/2014 | Bembridge et al. | |
| 2016/0016001 | A1 | 1/2016 | Loupis et al. | |
| 2018/0243582 | A1 | 8/2018 | Kaisha | |
| 2019/0373687 | A1 | 12/2019 | Williams et al. | |

OTHER PUBLICATIONS

Extended European Search Report dated May 25, 2023 in related European Application No. 20822634.0.

International Search Report and Written Opinion for related PCT application PCT/US2012/064198. International filing date Nov. 8, 2012.

Definition of flexible. Merriam-Webster Dictionary, retrieved on Dec. 13, 2013; Retreived from the internet: <http://www.merriam-webster.com/dictionary/flexible>.

Definition of deform. Merrima-Webster Dictionary, retrieved on Dec. 13, 2013; Retrieved from the internet: <http://www.merrima-webster.com/dictionary/deform>.

Daniel Barolet, M.D. "Light-Emitting Diodes (LEDs) in Dermatology", Seminars in Cutaneous Medicine and Surgery, vol. 27, pp. 227-238, 2008.

Daniel Barolet, et al., Importance of Pulsing Illumination Parameters in Low-Level-Light Therapy, Journal of Biomedical Optics, vol. 15, No. 4, pp. 048005-1-048005-8, 2010.

Supplementary European Search Report dated Jul. 23, 2015 for related European Application No. 12847625.6.

PCT International Search Report dated Sep. 11, 2020 in related PCT Application No. PCT/US2020/037586.

Biophotas, Inc. Introduces the Celluma POD Light Therapy Device—News Provided by BioPhotas, Inc., May 31, 2018. https://www.prnewswire.com/news-releases/biophotas-inc-introduces-the-celluma-pod-light-therapy-device-300657659.html.

PCT International Search Report dated May 24, 2021 in related PCT Application No. PCT/US2021/020023.

* cited by examiner

LIGHT THERAPY DEVICE AND METHOD FOR DELIVERY OF LIGHT THERAPY TO A BODY PART

RELATED APPLICATION

This is a continuation of copending U.S. patent application Ser. No. 15/980,277 filed May 15, 2018, which is a continuation of U.S. patent application Ser. No. 14/534,083 filed Nov. 5, 2014 and issued May 15, 2018 as U.S. Pat. No. 9,968,799, which is a continuation of U.S. patent application Ser. No. 13/672,554 filed Nov. 8, 2012 and issued Dec. 2, 2014 as U.S. Pat. No. 8,900,283, which claims priority to U.S. Provisional patent Application No. 61/557,319 entitled Shapeable Light Therapy Device and Method filed Nov. 8, 2011, the entirety of each such patent and application being expressly incorporated herein by reference.

FIELD OF THE INVENTION

The present invention relates generally to the fields of physics, electronics, biology and medicine and more particularly to devices and methods for delivering light therapy to humans or animals.

BACKGROUND

Light therapy (i.e., "phototherapy"), using various types of light, has been used or proposed for use in a number of cosmetic and therapeutic applications, including but not necessarily limited to improvement of skin elasticity, deterrence of skin aging, treatment of dermatological disorders (e.g., acne, psoriasis), healing of wounds, treatment of jaundice in newborns, and treatment of certain psychological conditions such as seasonal affective disorder (SAD) and certain sleep disorders. In some applications, light therapy is used alone while in others it is used in combination with drugs or agents (e.g., photo-sensitizing agents, photo-activating agents, agents which reduce skin opacity or improve light penetration through or into the skin, etc.). In some forms of light therapy, the subject is positioned in or near a device called a light therapy box. In other forms of light therapy, a light emitting device is positioned on or near a particular are of the body to be treated.

One example of a light emitting device that is positionable on or near a particular are of the body to be treated is described in United States Patent Application Publication No. 2011/0144724 (Benedict) entitled Portable Phototherapy Device and Method for Using a Portable Phototherapy Device, a copy of which is appended to and forms a portion of U.S. Provisional patent Application No. 61/557,319, to which this application claims priority. The entire disclosure of United States Patent Application Publication No. 2011/0144724 (Benedict) is also expressly incorporated herein by reference.

Light emitting phototherapy devices of the prior art have not been optimal for all potential applications. For example, at least some light emitting phototherapy devices of the prior art have lacked sufficient flexibility characteristics to allow them to be formed by had into various alternative shapes (e.g., including shapes that have tight radii of curvature and/or complex curvatures) without damaging the device and/or have required the use of a strap or other shape-retaining apparatus to hold the device in a desired shape during use. In general, this lack of formability can result in some or all of the light emitters of the device being positioned at non-optimal distances from the affected body surface during treatment. The development of new light emitting phototherapy devices having improved or different formability may improve the potential efficacy of the phototherapy provided by enabling the device to be pre-formed to a shape that causes many or all of the light emitters on the device to be within a therapeutically optimal distance from the affected body surface.

Accordingly, there remains a need in the art for the development of new or modified phototherapy devices that incorporate modifications and improvements which render them advantageous over the prior art.

SUMMARY OF THE INVENTION

The present invention provides new light therapy devices and methods as well as modifications, improvements and additions that may be incorporated into prior light therapy devices, such as those described in United States Patent Application Publication No. 2011/0144724 (Benedict). Additionally, certain aspects, details, attributes and elements of the invention may be understood from the examples shown in accompanying FIGS. 1-20 and described below.

In accordance with one aspect of the present invention, there is provided a light therapy device that may be substantially the same as that described in United States Patent Application Publication No. 2011/0144724 (Benedict) but which is capable of being formed into and retaining a desired shape (e.g., a curved or twisted shape) without the need for strap(s) or other restraining apparatus to hold the device in the desired shape. For at least some applications, the improved formability of the devices of the present invention enables such devices to be pre-formed to various shapes to ensure that many or all of the light emitters on the device will be within a therapeutically optimal distance (in some cases—as close as possible without touching) from the affected body surface. By positioning the light emitters within the therapeutically optimal distance from the body surface, factors such as the depth to which therapeutic wavelength(s) of light penetrate the subject's body.

In accordance with another aspect of the present invention, there are provided light therapy devices that include light emitters (e.g., LEDs) which emit light at wavelength(s) outside of human visible range (referred to herein as "non-visible light"), wherein the device includes one ore more indicator(s) to indicate to a user of the device when the non-visible light is being emitted. For example, a light therapy device of the present invention may include an array of infrared, red and blue LEDs wherein each LED(s) emits light in accordance with one or more programmed light therapy protocols. In such device, one or more indicator LED's of a different visible color (e.g., green LED(s)) may be included in the array and the device may be programmed to cause such indicator LED(s) to illuminate when the infrared LEDs are emitting non-visible light.

In accordance with one specific embodiment of the invention, there is provided a system which comprises a) a pad (e.g., panel, sheet, etc.) that is positionable on or near a portion of the body or a human or animal subject and b) at least one light emitter positioned on or in the pad and operative to deliver a light therapy session by casting light from the pad onto or into said portion of the body. At least a portion of the pad is formable into alternative configurations (e.g., curved or twisted configurations) and, when formed into a particular alternative configuration, will retain that alternative configuration during a subsequent light therapy session without the need for straps or other retainer members to hold the device in such alternative configuration. In this manner the device may be custom-formed to a desired configuration at the time of each use. For example, the device may be formed to correspond (e.g., fit upon or have an analogous configuration to) the anatomical shape of the portion of a human or animal's body to which light therapy is to be delivered. In some embodiments, substantially the entire pad may be shapeable while in other embodiment(s) only one or more portions of the pad may be shapeable. In some embodiments, the pad may have a plurality of shapeable regions, one or more of which have different forming properties (e.g., flexibility, rigidity, shape memory, elasticity, etc.) than one or more other of shapeable regions. For example, in some embodiments, end regions of the device may be shapeable to more precise or smaller curves than a mid-region of the device. To have the desired formability, the device may be constructed in any suitable manner. For example, in some embodiments substantially the entire pad may be formed of plastically deformable material (e.g., memory material, bendable material, malleable material, shapeable material, etc.). In other embodiments the pad may comprise a composite or layered structure that includes flexible and plastically deformable components or layers, in combination. One non-limiting example of such construction is shown in the accompanying FIGS. 1-20 and described in detail herebelow.

In accordance with another aspect of the invention, there is provided a method for delivering light therapy to a human or animal subject. This method generally comprises the steps of: A) causing a device of the foregoing character to be positioned on or near the body of the subject and B) using the device to deliver light to the subject. Step A of this method may include forming of the device to a desired configuration and causing the device to be positioned on or near the body of the subject while it is formed in that desired configuration. As described above, the desired configuration to which the device is formed may correspond to the anatomical shape of the selected body portion to which light therapy is to be delivered. When using an embodiment of the device that is programmed for operation in alternative light treatment modes, Step B of the method may include selecting the desired light treatment mode in which therapy is to be delivered. When using an embodiment of the device that is programmed to deliver light therapy in either non-modulated (e.g., non-pulsed) or modulated (e.g., pulsed) form, Step B of the method may include selecting either non-modulated or modulated light. The available treatment modes and/or modulation options may be selected for use in treating different pathological or cosmetic conditions and/or for varying the depth of penetration of the desired wavelength(s) of light into the subject's body. Examples of different therapeutic effects that may be achieved by selection of different treatment modes (e.g., red light vs. blue light vs. infrared light) are described in Bartolet, D., *Light-Emitting Diodes (LEDs) in Dermatology*; Seminars in Cutaneous Medicine and Surgery, Vol. 27: pp. 227-238 (2008). Examples of different therapeutic effects that may be achieved by selection of different modulation (e.g., pulsation or non-pulsation) characteristics are described in Bartolet, D., *Importance of Pulsing Illumination Parameters in Low-Level-Light Therapy*; Journal of Biomedical Optics, Vol. 15, No. 4: pp. 048001-048005 (2010).

DETAILED DESCRIPTION AND EXAMPLES

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way. This example refers to the accompanying FIGS. 1-20.

Figure 1:
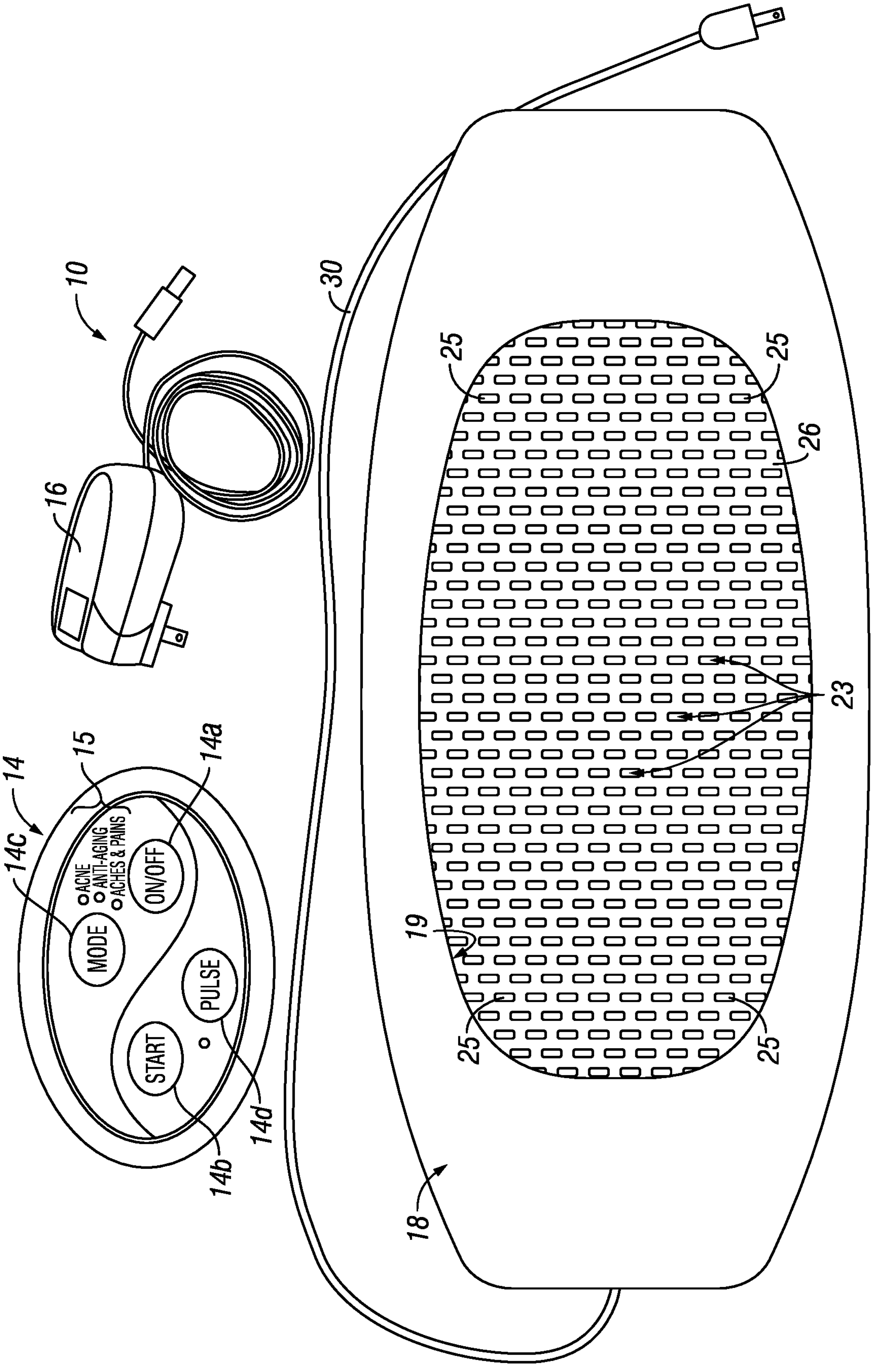
FIG. 1 shows one example of a light therapy system comprising a shapeable light therapy device (front view), power source and controller.
Figure 2:
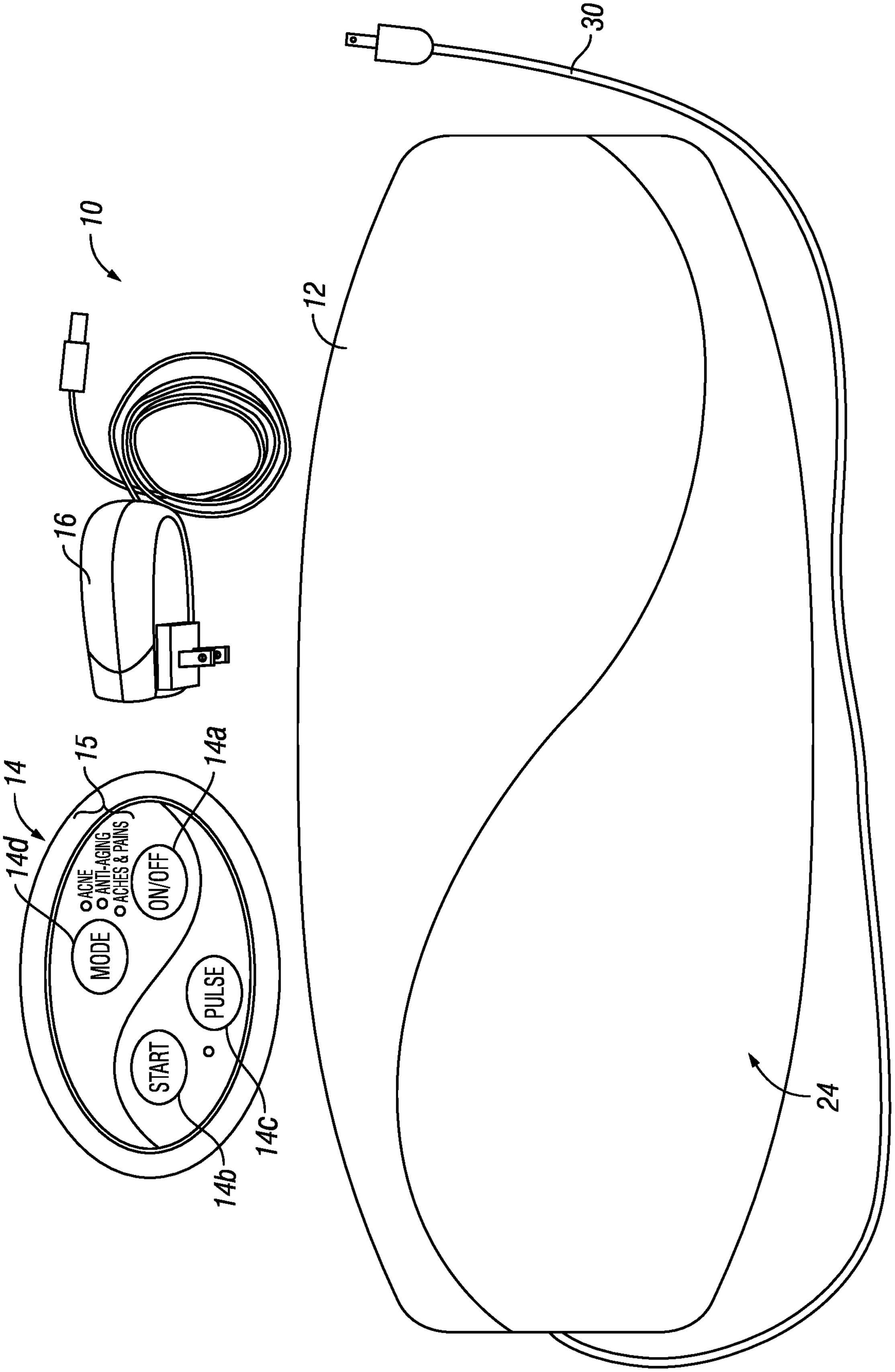
FIG. 2 also shows the light therapy system of FIG. 1 with a rear view of the shapeable light therapy device.

FIGS. 1 and 2 show one non-limiting example of a system 10 of the present invention. This system 10 includes at least one shapeable pad light emitting apparatus 12, a controller/user interface 14 and a power supply 16. In some applications the controller/user interface 14 may be connected to a single shapeable pad light emitting apparatus 12. In other applications, the controller/user interface 14 may be connected to, and used to simultaneously control, more than one shapeable pad light emitting apparatus 12. Such simultaneous use of more than one shapeable pad light emitting apparatus 12 may be desirable in instances where more than one area of a subject's body is being treated. In FIG. 1, the shapeable pad light emitting apparatus 12 in seen in front view while in FIG. 2 a rear view of the shapeable pad light emitting apparatus 12 is shown.

In general, the power source 16 may be any suitable type of power source. In the particular non-limiting example shown in these drawings, the power source 16 comprises a universal power source that may be plugged into standard wall power outlets in various geographic regions of the world to supply power to the shapeable pad light emitting apparatus 12 and controller/user interface. In the example shown, the shapeable pad light emitting apparatus 12 has a control cable 30 that is adapted to be alternately connected to and disconnected from the controller/user interface 14. In some such embodiments, the controller/user interface 14 may have multiple jacks or connector sites so that it may be connected to, and used to control, more than one shapeable pad light emitting apparatus 12. In other embodiments, the control cable 30 of at least one shapeable pad light emitting apparatus 12 may be permanently connected to the controller/user interface.

In general, the controller/user interface 14 may comprise a suitable microprocessor, circuit board and user interface which communicates by wired or wireless connection with the shapeable pad light emitting apparatus 12 to provided on/off, mode and pulsation control of the light emitted by the LEDs of the shapeable pad light emitting apparatus 12. In some embodiments, the controller/user interface 14 may be programmed to simultaneously control more than one shapeable pad light emitting apparatus 12 when desired. In the particular non-limiting example shown in the drawings, the controller/user interface includes an on/or button 14*a*, a mode selection button 14*c*, selected mode indicator lights 15, a treatment start button 14*b* and a pulsation on/pulsation off button 14*d*. Non-limiting examples of specific electrical circuitry and components usable in this controller/user interface 14 are shown in the schematics and diagrams of FIGS. 19-20.

Figure 3:
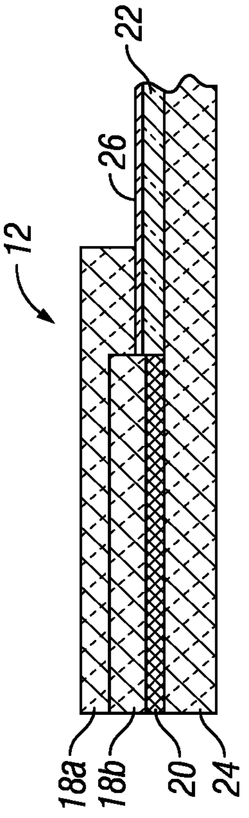
FIG. 3 shows a sectional view of a portion of the shapeable light therapy device of FIG. 1.
Figure 4:
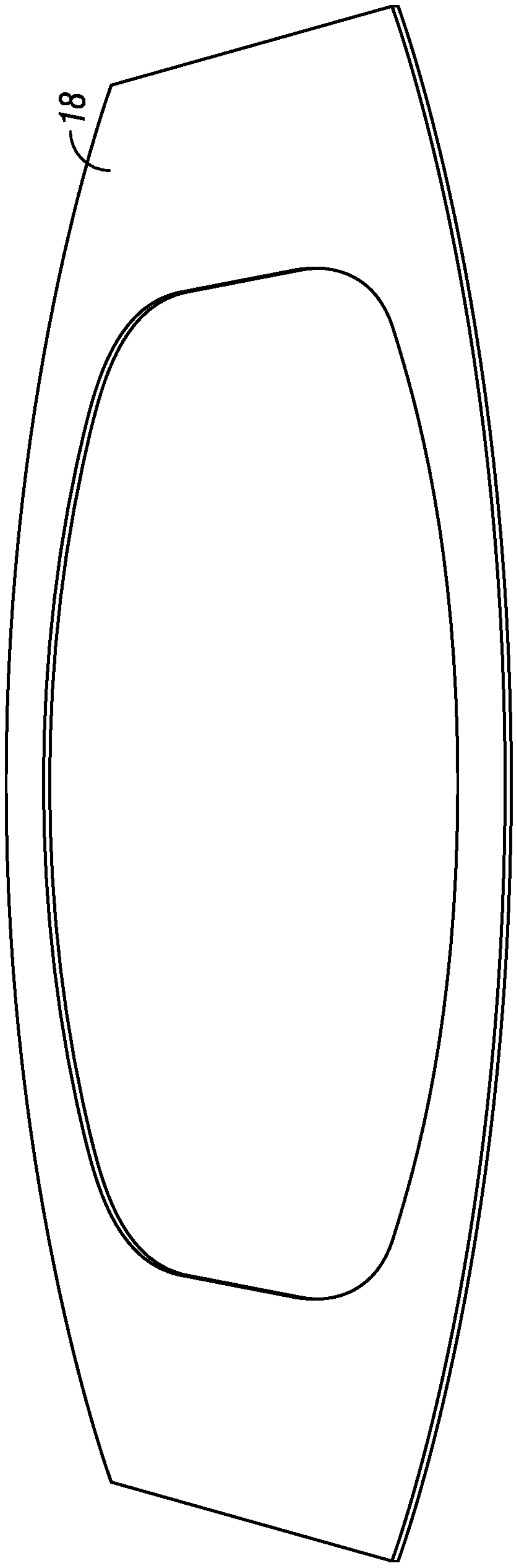
FIG. 4 shows a top flexible pad component used in the manufacture of the shapeable light therapy device of FIG. 1.

In general, the shapeable pad light emitting apparatus 12 of this example may comprise a number of components affixed in a stacked array as shown in the cross sectional view of FIG. 3. These components include a front flexible pad layer 18 having a central aperture 19 formed therein, a plastically deformable (e.g., bendable, malleable, shapeable) layer 20 which also has a central aperture 19 formed therein, at least one flexible circuitry layer 22 having light emitting diodes (LEDs) 23 positioned thereon and a rear flexible pad member 24. Examples of specific electrical circuitry and components usable in the circuitry layer 22 are shown in the schematics and diagrams of FIGS. 13-18. In the particular non-limiting example shown in FIG. 1, the LEDs 23 include a multiplicity of therapeutic light emitting LEDs including infrared, red and blue LEDs as well as one ore more indicator LEDs 25 comprising green LEDs which emit light only when the infrared LEDs are illuminated. In this manner, the visible green light emitted by the indicator LEDs signals to the user and/or the subject being treated when the non-visible infrared LEDs are emitting therapeutic light.

As may be appreciated from the cross-sectional view of FIG. 3, in some embodiments, the front flexible pad member 18 may be formed of two layers of flexible plastic foam 18*a* and 18*b*, in juxtaposition to one another. These components affixed to one another in a stacked array such that light emitted by the LEDs will pass through the central aperture of the front flexible pad layer 18. A translucent shield or barrier 26 may extend over the front of the flexible circuitry layer 22 thereby preventing the LEDs and any other electronic components on the front side of the flexible circuitry layer 22 from directly contacting objects or body surfaces and/or to allow hygienic cleansing of the device, while allowing the emitted light to pass through the translucent shield or barrier 26. Optionally, in some embodiments, all or just a portion (e.g., a peal off front surface film layer) of the translucent shield or barrier 26 may be disposable and/or replaceable between uses of the device 10.

The flexible circuitry layer 22 may comprise one or more flexible circuit boards. Specifically, in this example, the flexible circuitry layer 22 may comprise a flexible printed circuit board having the LEDs and possibly other components such as resistors. A second printed circuit board comprising firmware embedded in microprocessor logic circuitry may be housed in the user interface 14 or any other component connected to the device 10. Also, in this example, the LEDs comprise infrared, red and blue LEDs which, respectively, deliver infrared light having a wavelength of, or of about, 880 nm; red light having a wavelength of, or of about, 640 nm or blue light having a wavelength of, or of about, 465 nm.

Figure 7:
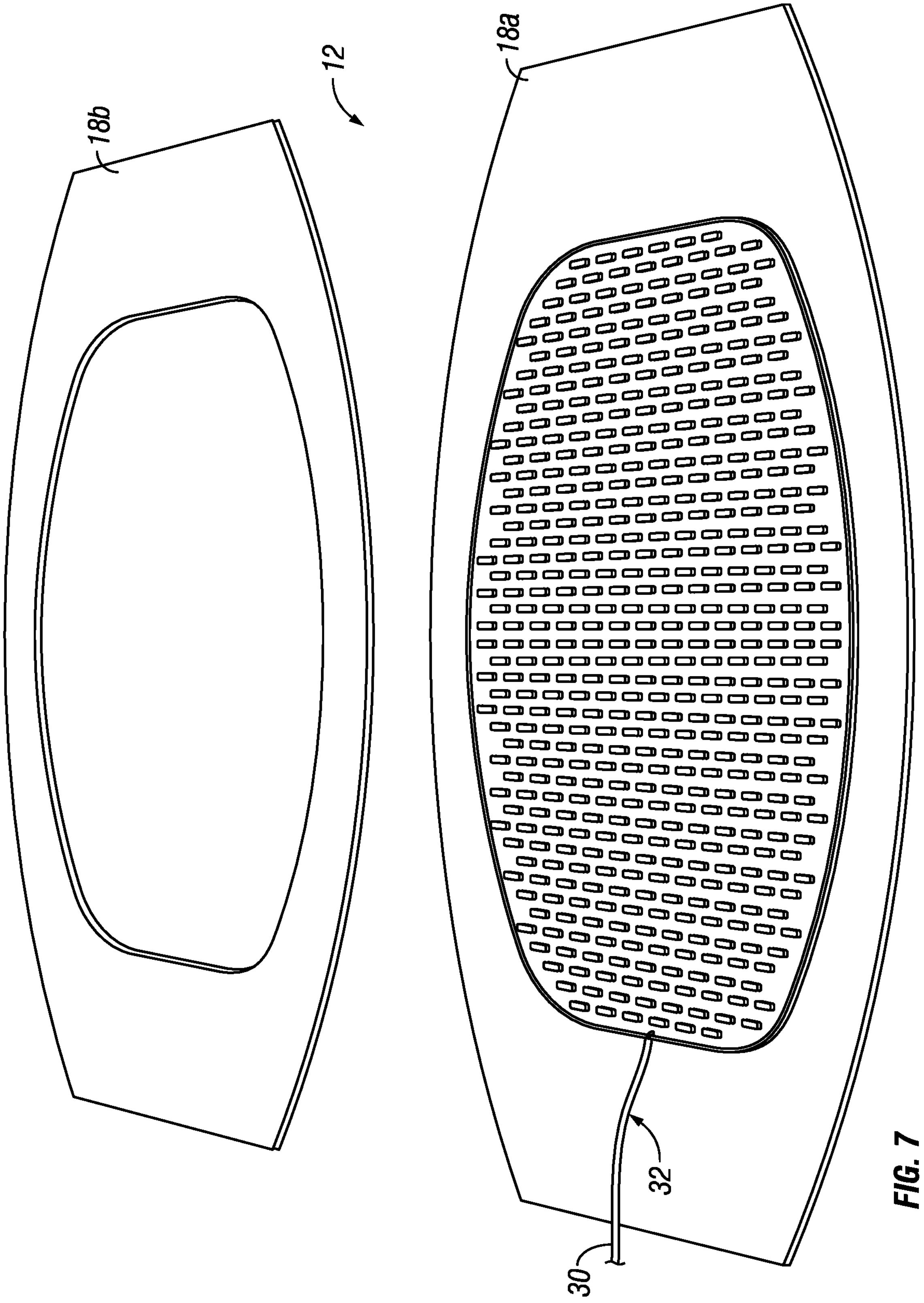
FIG. 7 shows an exploded view of various component layers of the shapeable light therapy device of FIG. 1.
Figure 8:
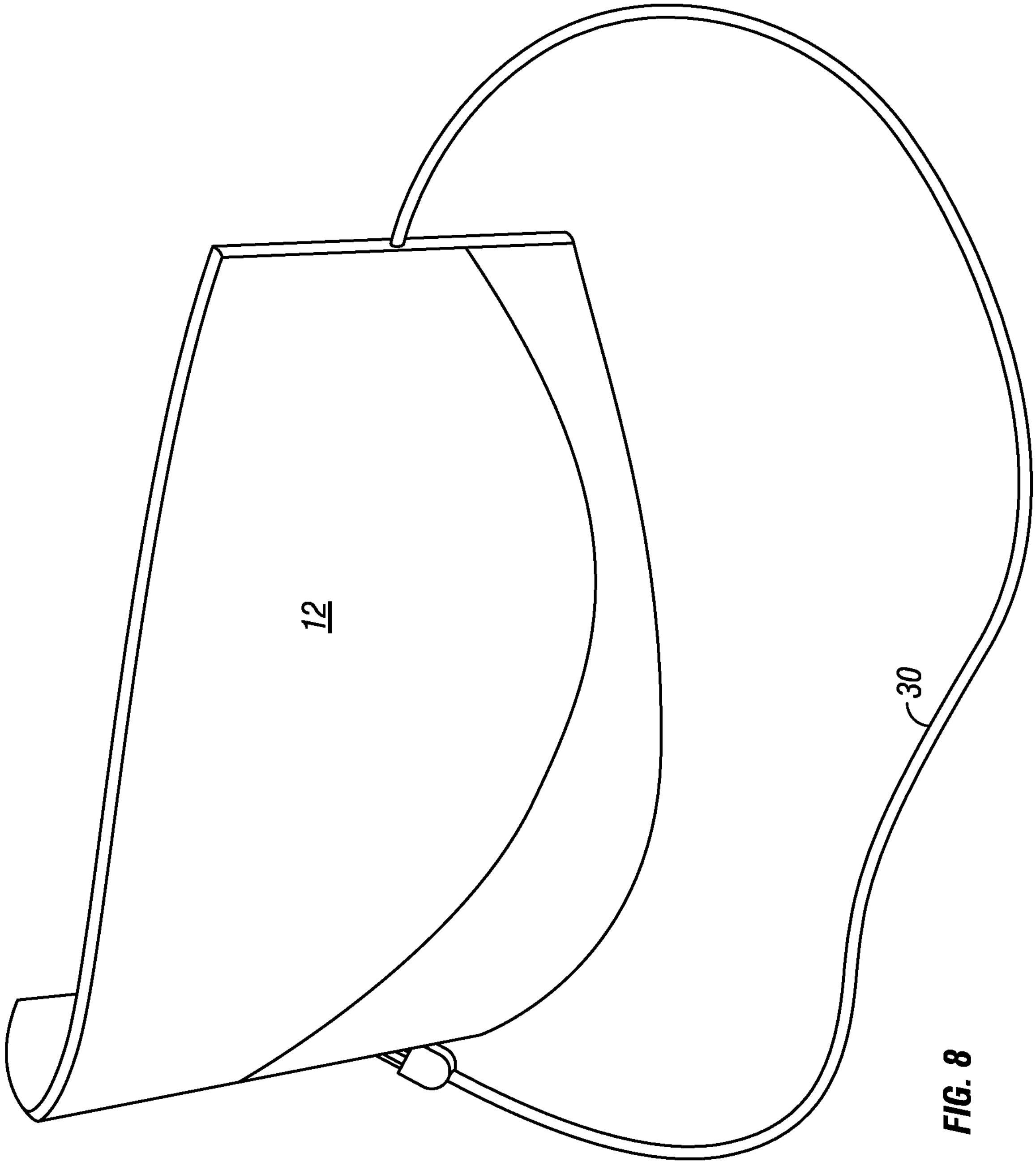
FIG. 8 is a rear view of the fully assembled shapeable light therapy device of FIG. 1 disposed in a first curved shape.
Figure 9:
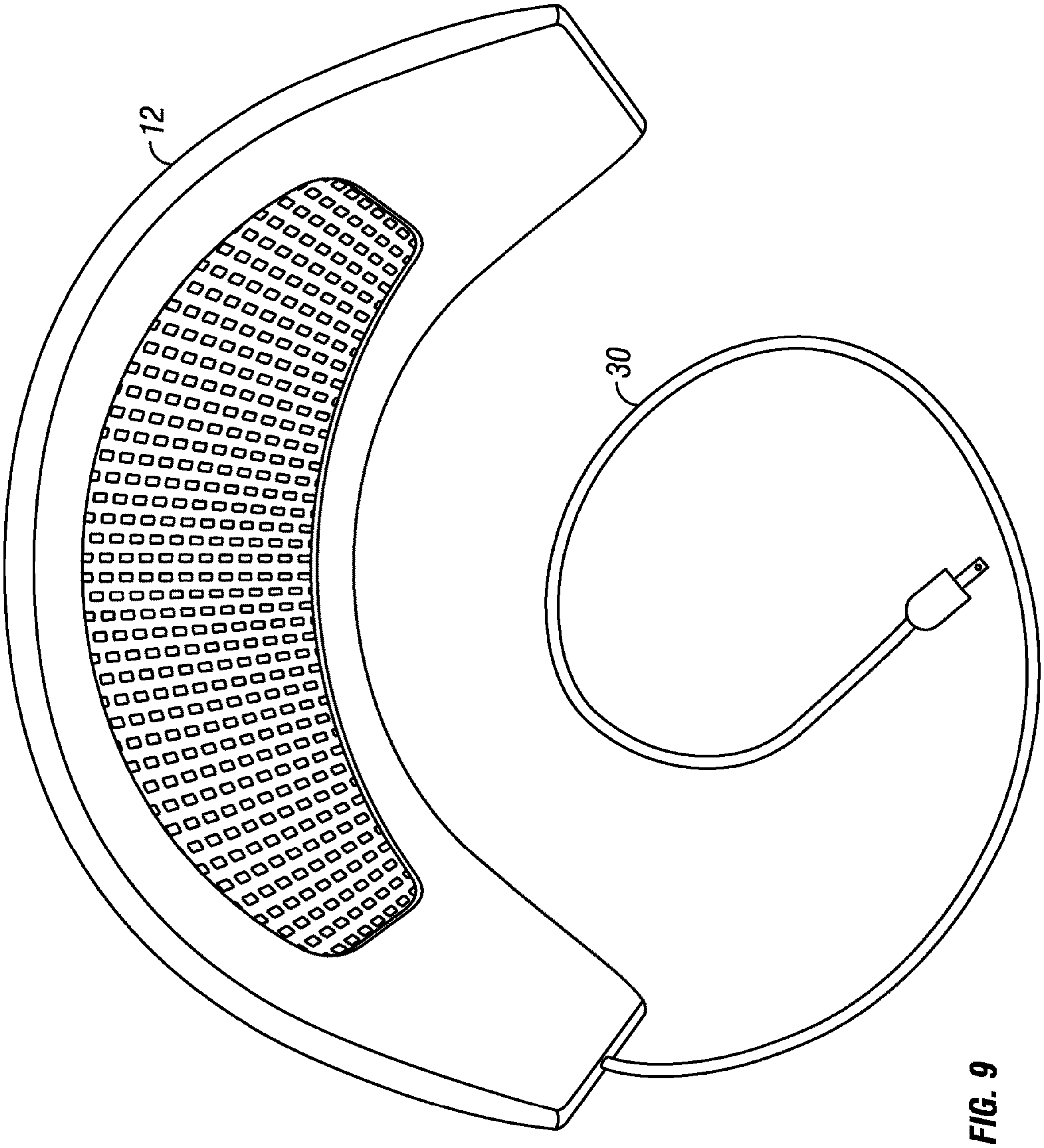
FIG. 9 is a front view the fully assembled shapeable light therapy device of FIG. 1 disposed in the first curved shape.
Figure 10:
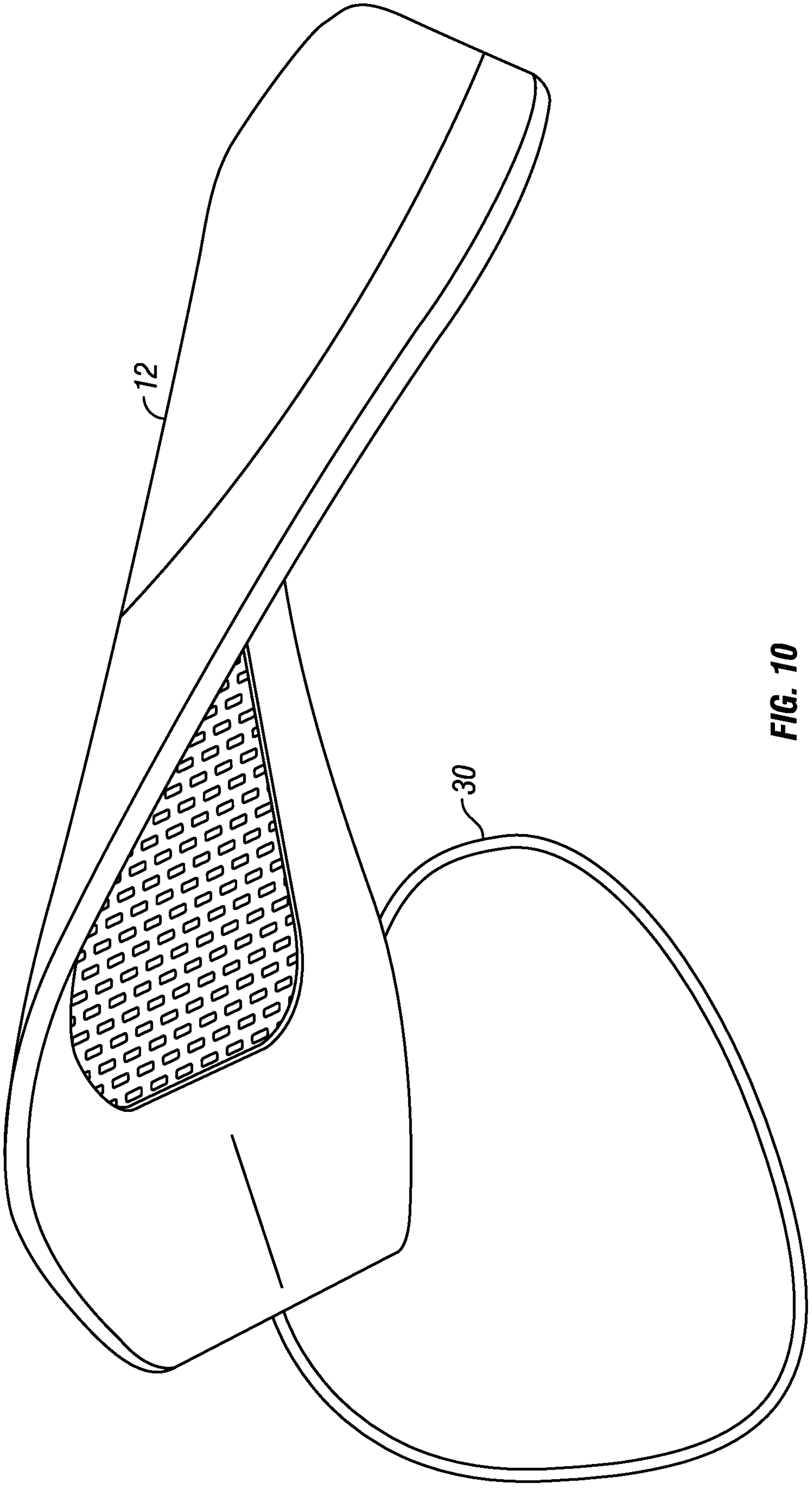
FIG. 10 is a front view of the fully assembled shapeable light therapy device of FIG. 1 disposed in a twisted shape.
Figure 11:
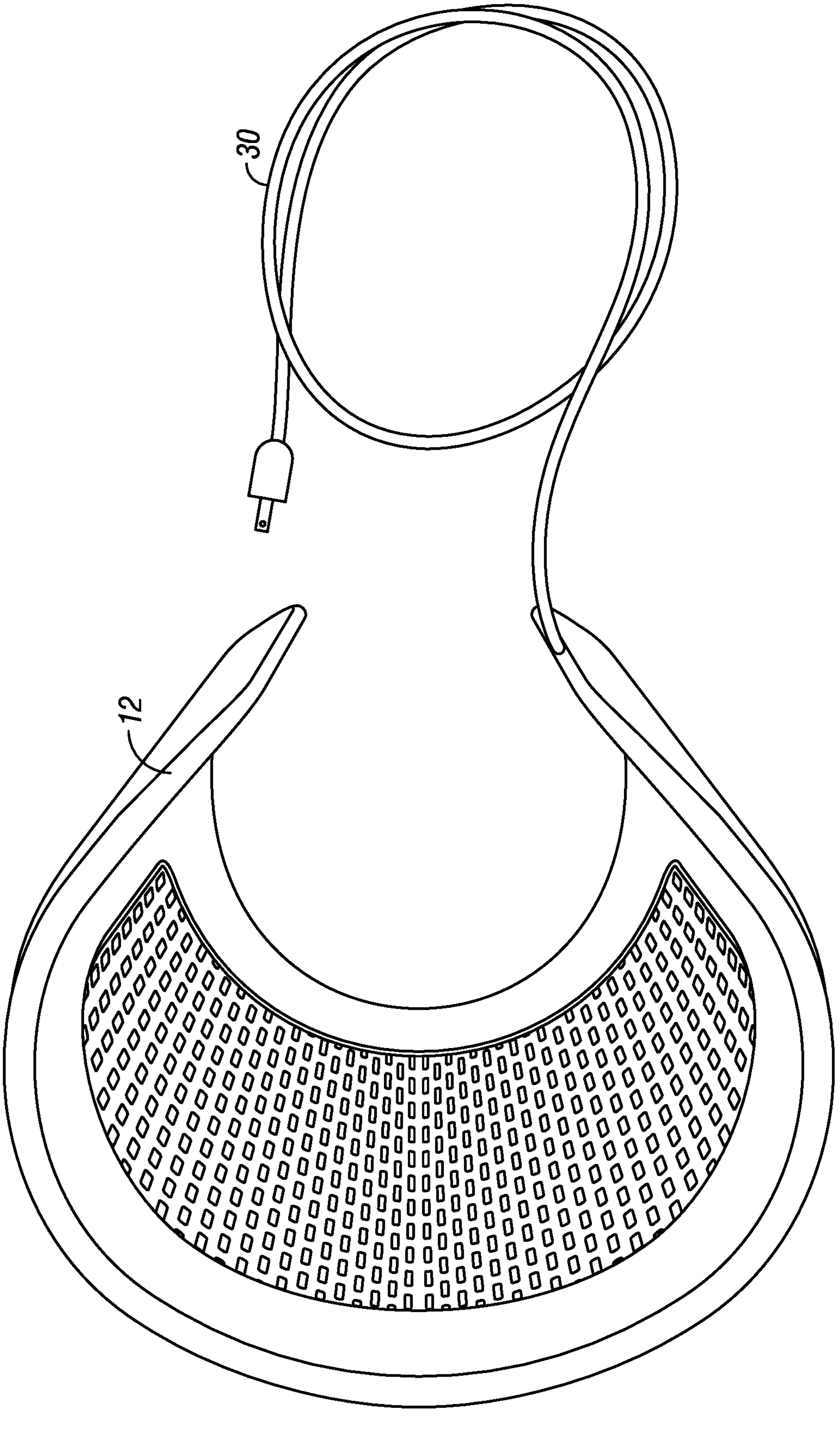
FIG. 11 is a front view of the fully assembled shapeable light therapy device of FIG. 1 disposed in a second curved shape.

As seen in FIG. 7, a control cable 30 is connected to the flexible circuitry layer 22. Such control cable 30 may extend through a passage channel 32 formed in the rear layer 18*a* of the front flexible pad member 18. The front layer 18*b* may then be placed over top of the rear layer 18*a* to encase the control cable 30 within the channel 32.

Figure 5:
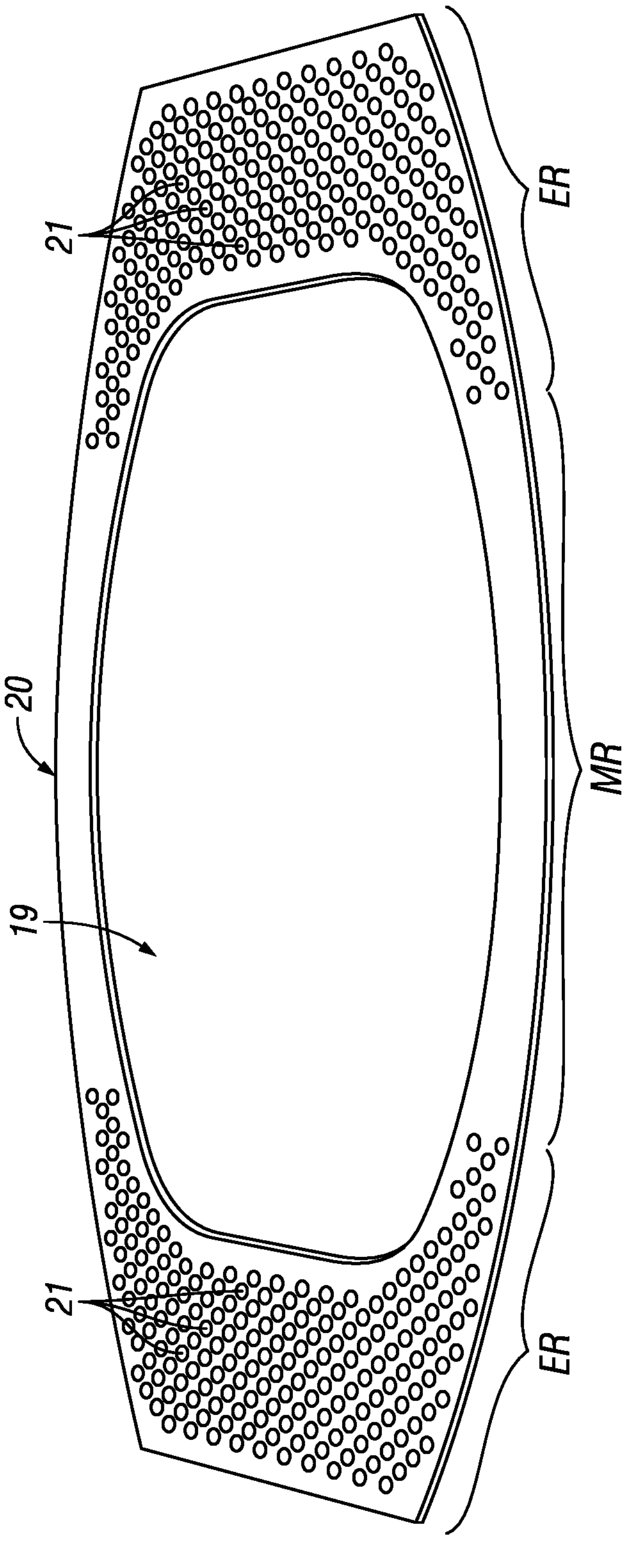
FIG. 5 shows a plastically deformable component used in the manufacture of the shapeable light therapy device of FIG. 1.
Figure 6:
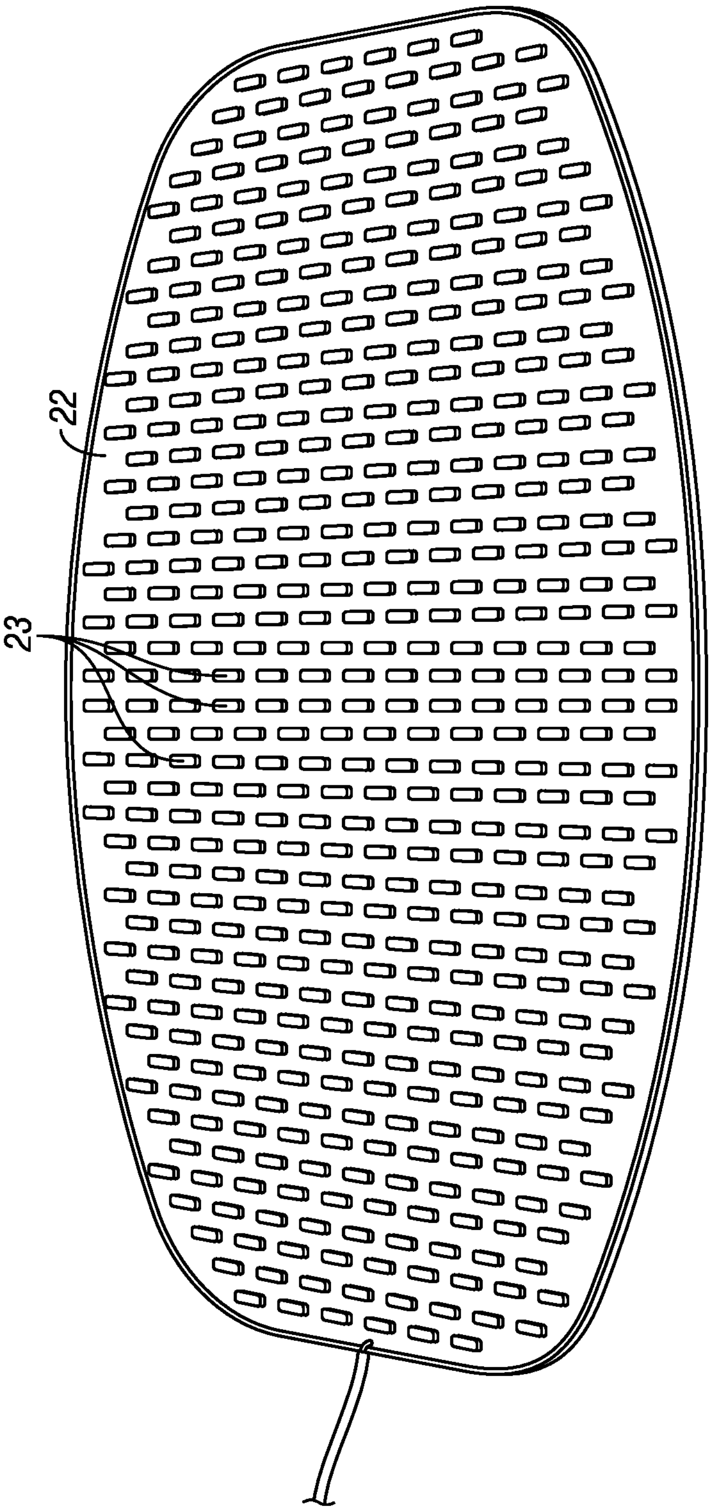
FIG. 6 shows a flexible circuitry layer component of the light therapy device of FIG. 1.

As seen in FIG. 5, in this example, the plastically deformable layer 20 is formed of a plastically deformable material (e.g., aluminum or other suitable metal, deformable memory plastic, etc.) that is flexible enough to be deformed to a desired configuration by hand while also having sufficient shape memory to retain the configuration to which it has been deformed during subsequent use of the device for delivery of a light therapy session. This metal sheet has end regions with perforations 21 formed therein and a non-perforated mid-region on either side of the central aperture 19. The size, number and spacing of the perforations 21 controls the forming properties (e.g., flexibility, rigidity, shape memory, elasticity, etc.) of the end regions and lessens the amount of force required to change the shape of those regions, thereby enabling a user to hand-shape the device as desired. For example, these perforations 21 in the plastically deformable layer 20 may render the end regions of the device 10 shapeable to curved shapes that have tighter or different radii of curvature than would be possible if such perforations 21 were not present. In this manner, regionalized perforations 21 are used to control the relative deformability and memory of various regions of the device 10. In this example, the perforations 21 allow the ends of the device 10 to be bent to form "feet" at either end of the device so that when the mid-region of the device is curved, the device will form an arch-like structure at a desired height over an underlying surface and/or body part. Also, in this example, the perforations 21 allow the use of a metal sheet that sufficiently thick enough to impart the desired structural integrity and forming properties to the relatively narrow portions on either side of the central aperture 19 in the mid-region, without causing the end regions to be too stiff or too difficult to bend or form to the desired shape(s).

Figure 12:
FIG. 12 shows a shapeable light therapy device of the present invention in the first curved shape positioned over the face and neck of a human subject so as to apply light therapy to the subject's face and neck.
Figure 13:
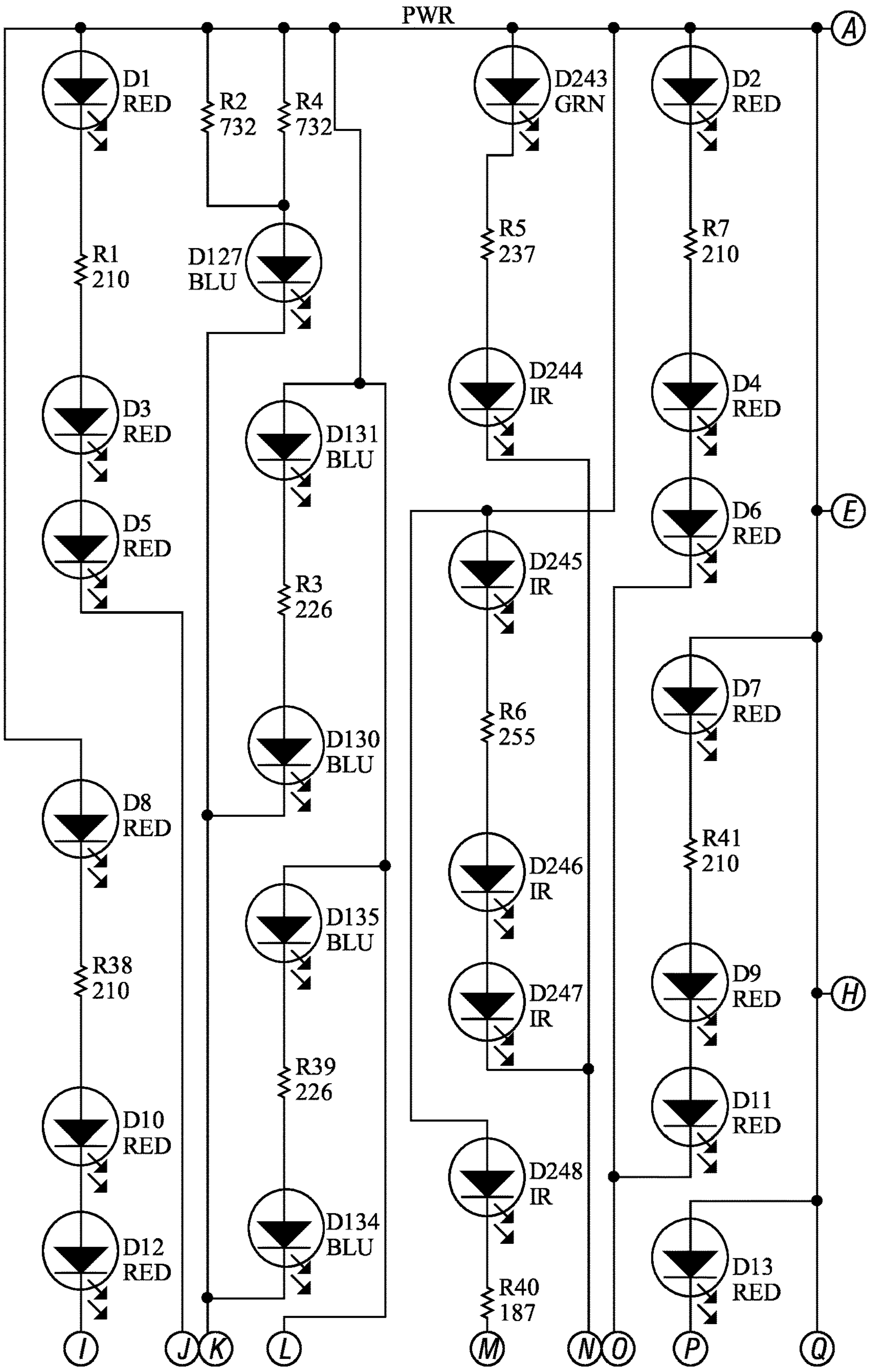
FIG. 13 is a schematic of a first portion of an LED array useable in the shapeable light therapy device of FIG. 1.
Figure 13:
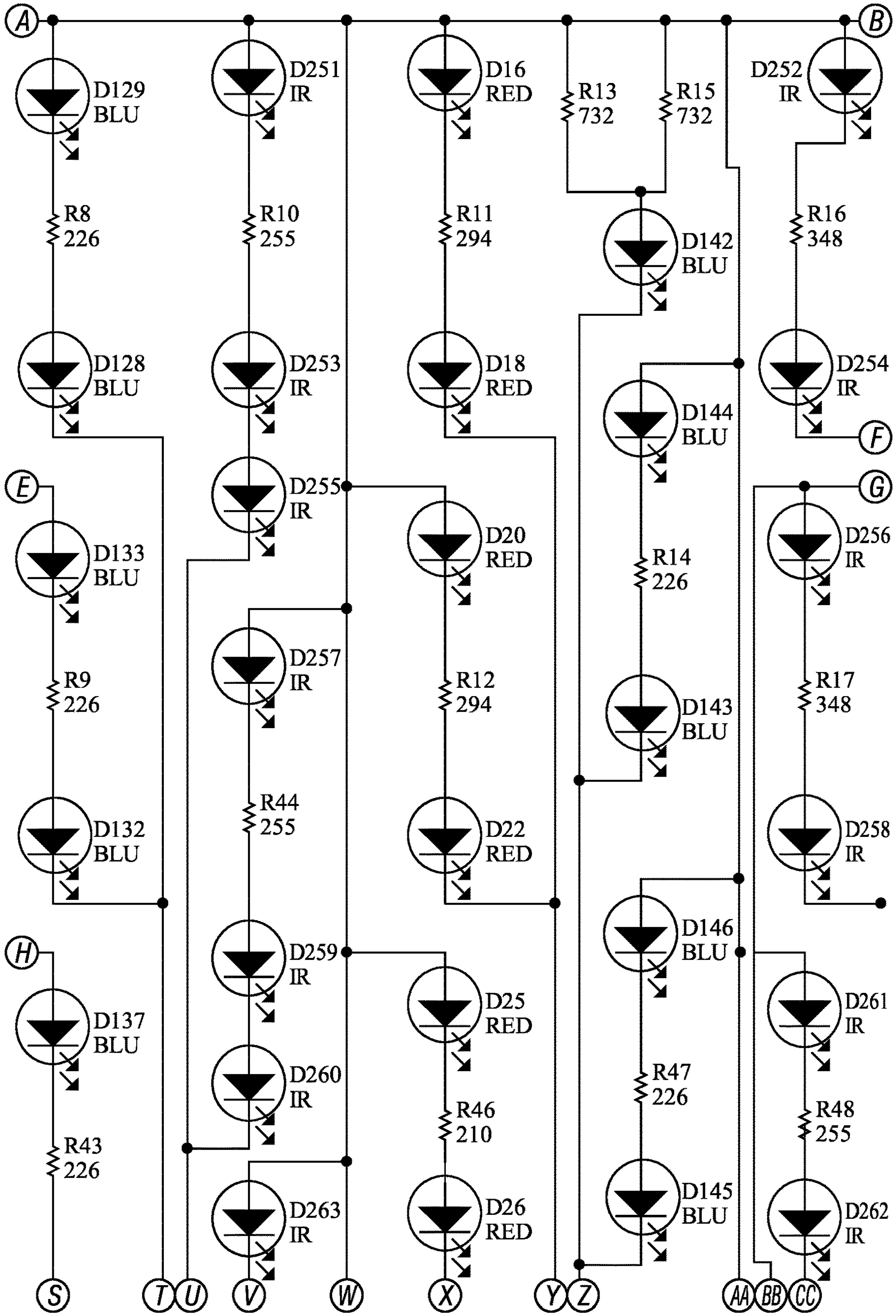
Figure 13:
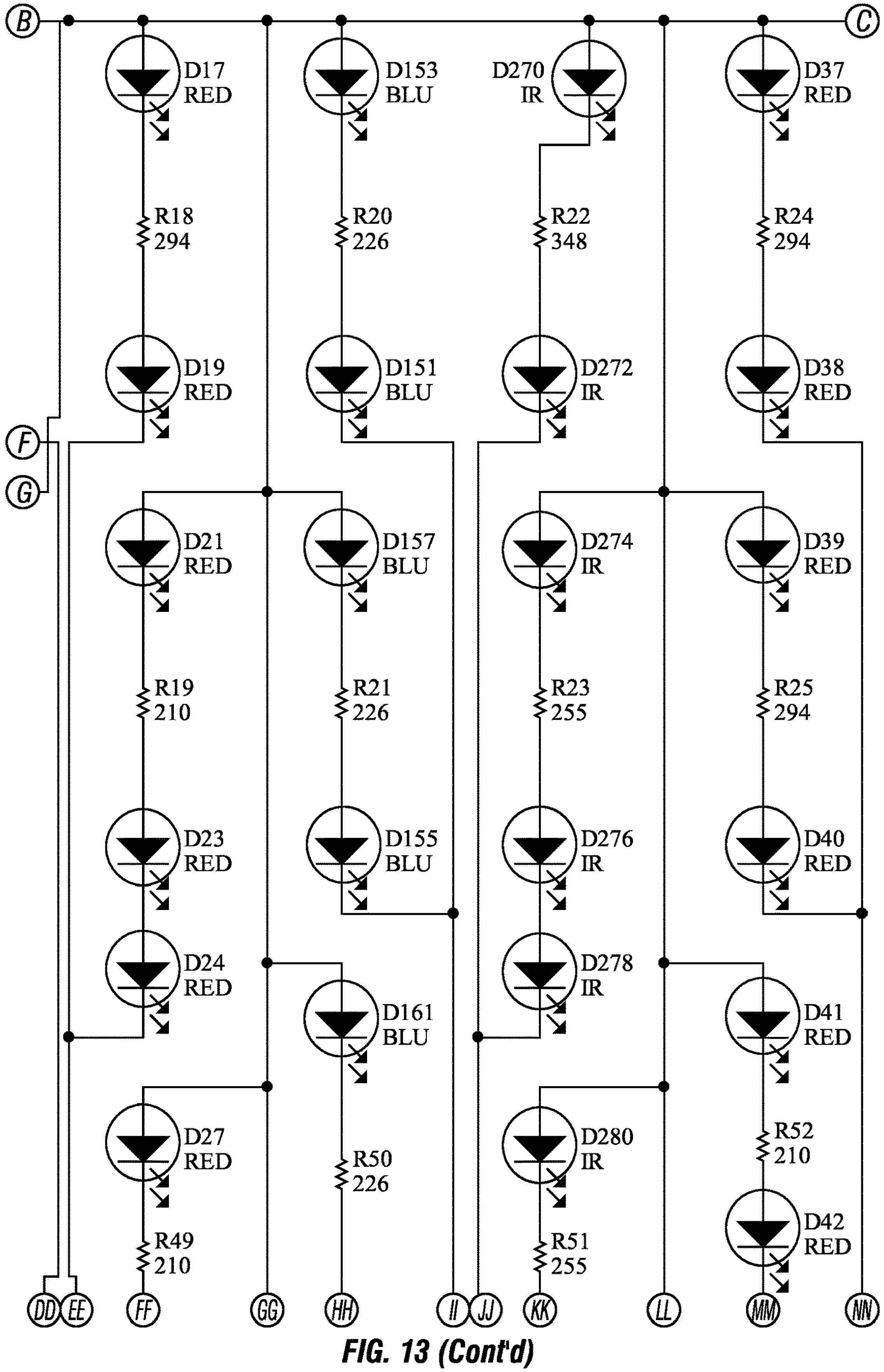
Figure 13:
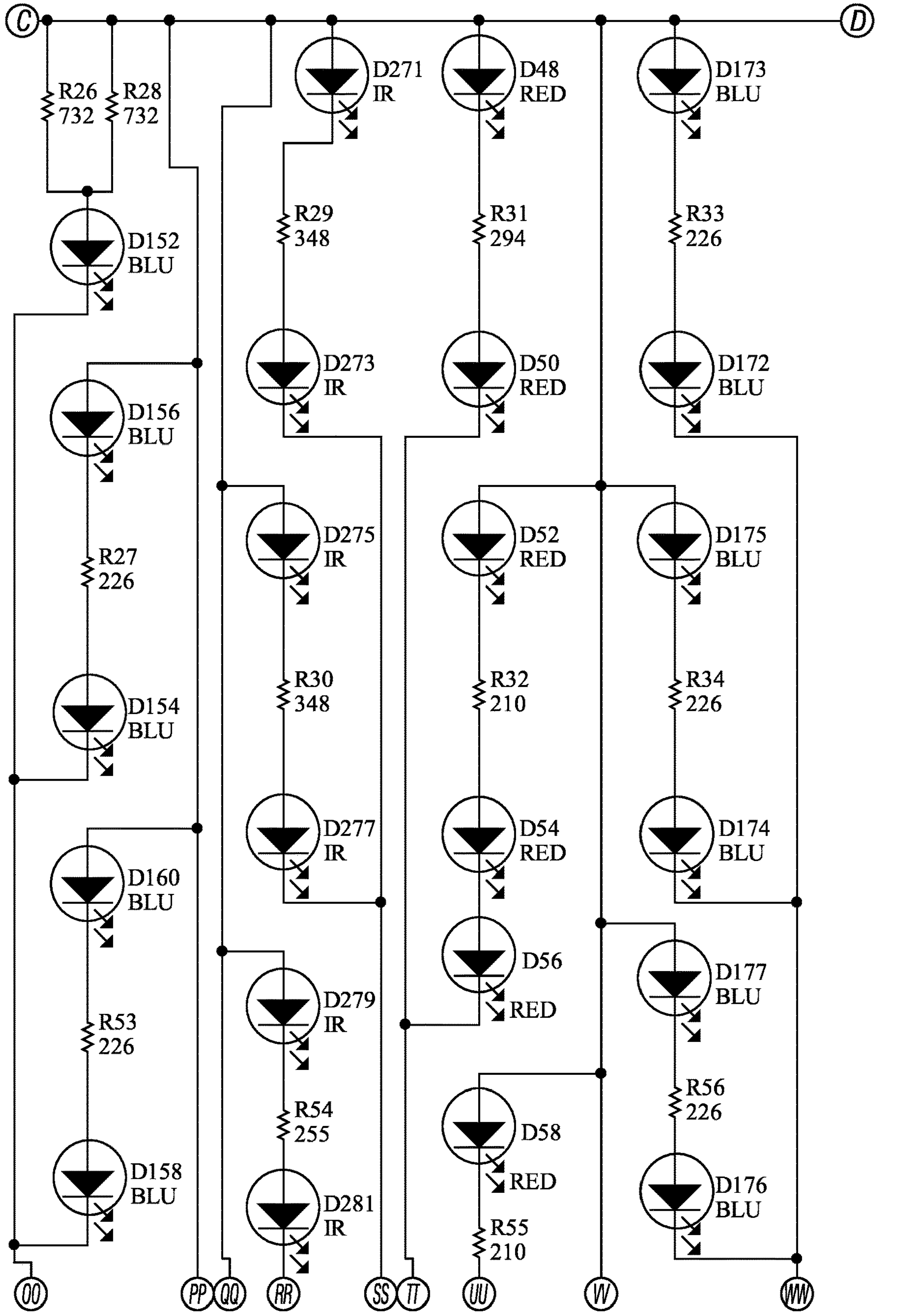
Figure 13:
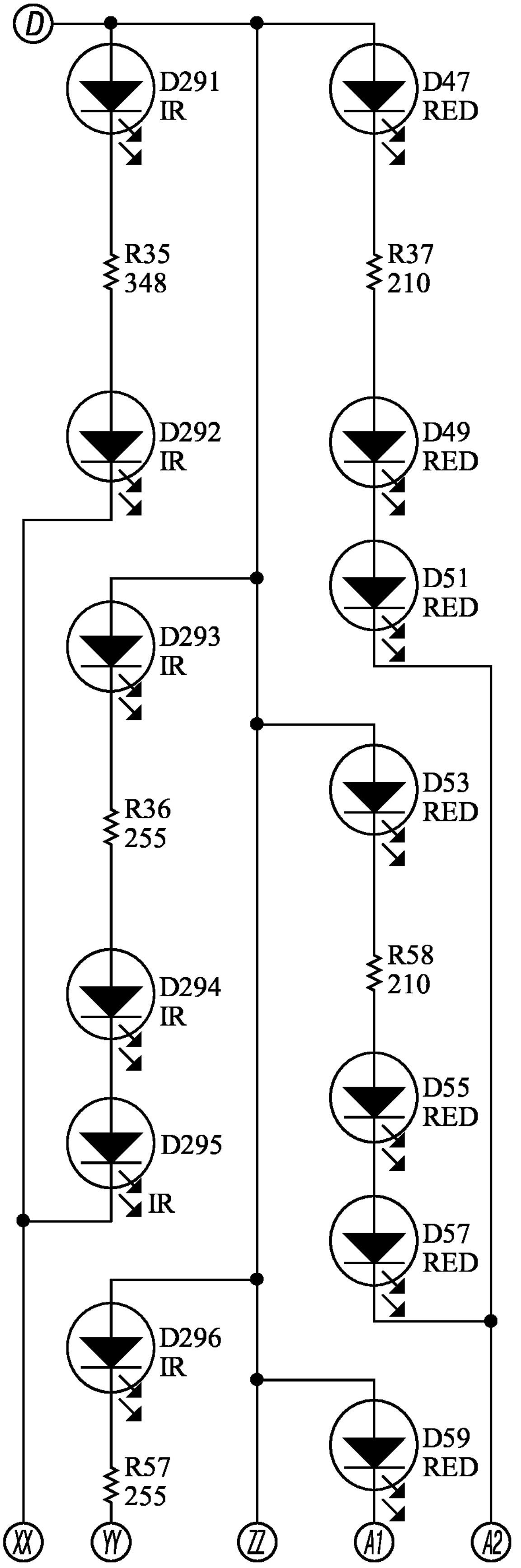
Figure 13:
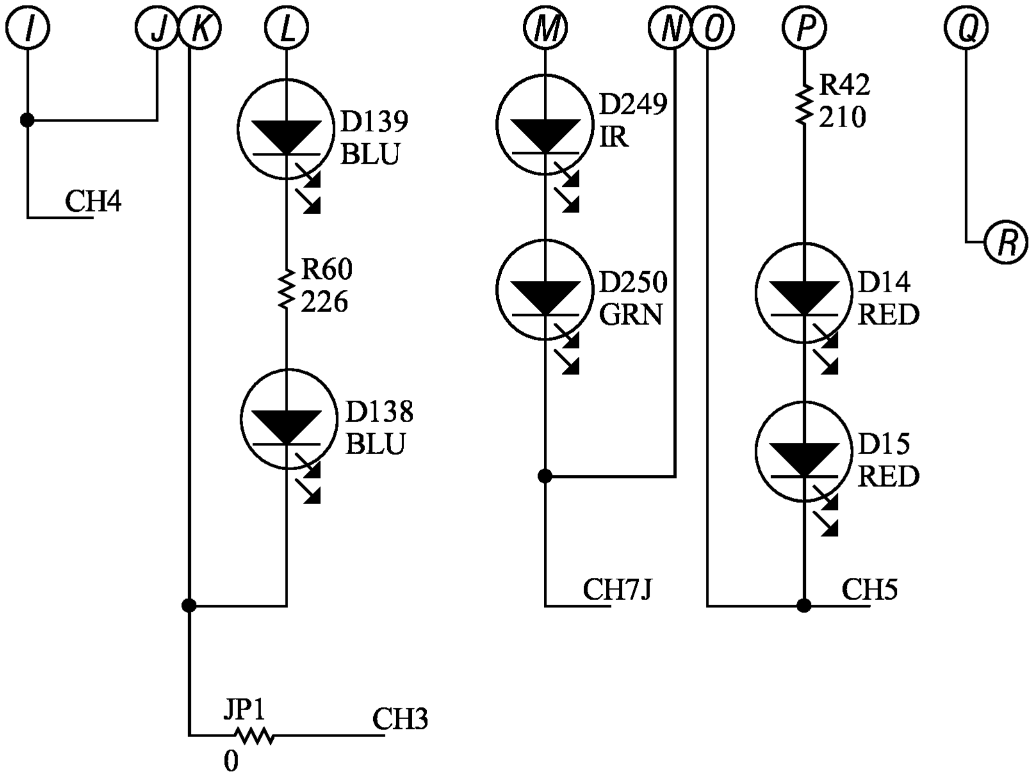
Figure 13:
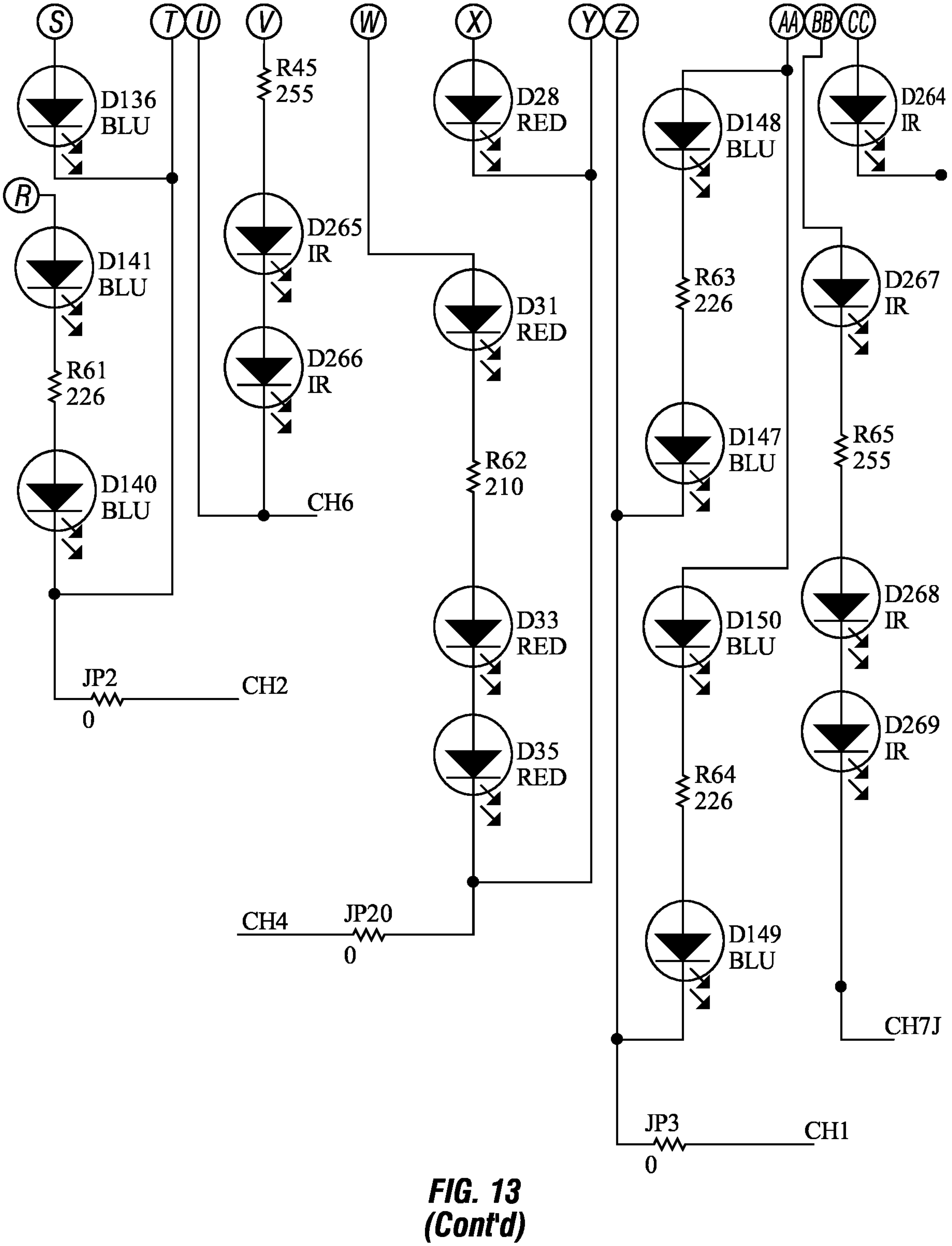
Figure 13:
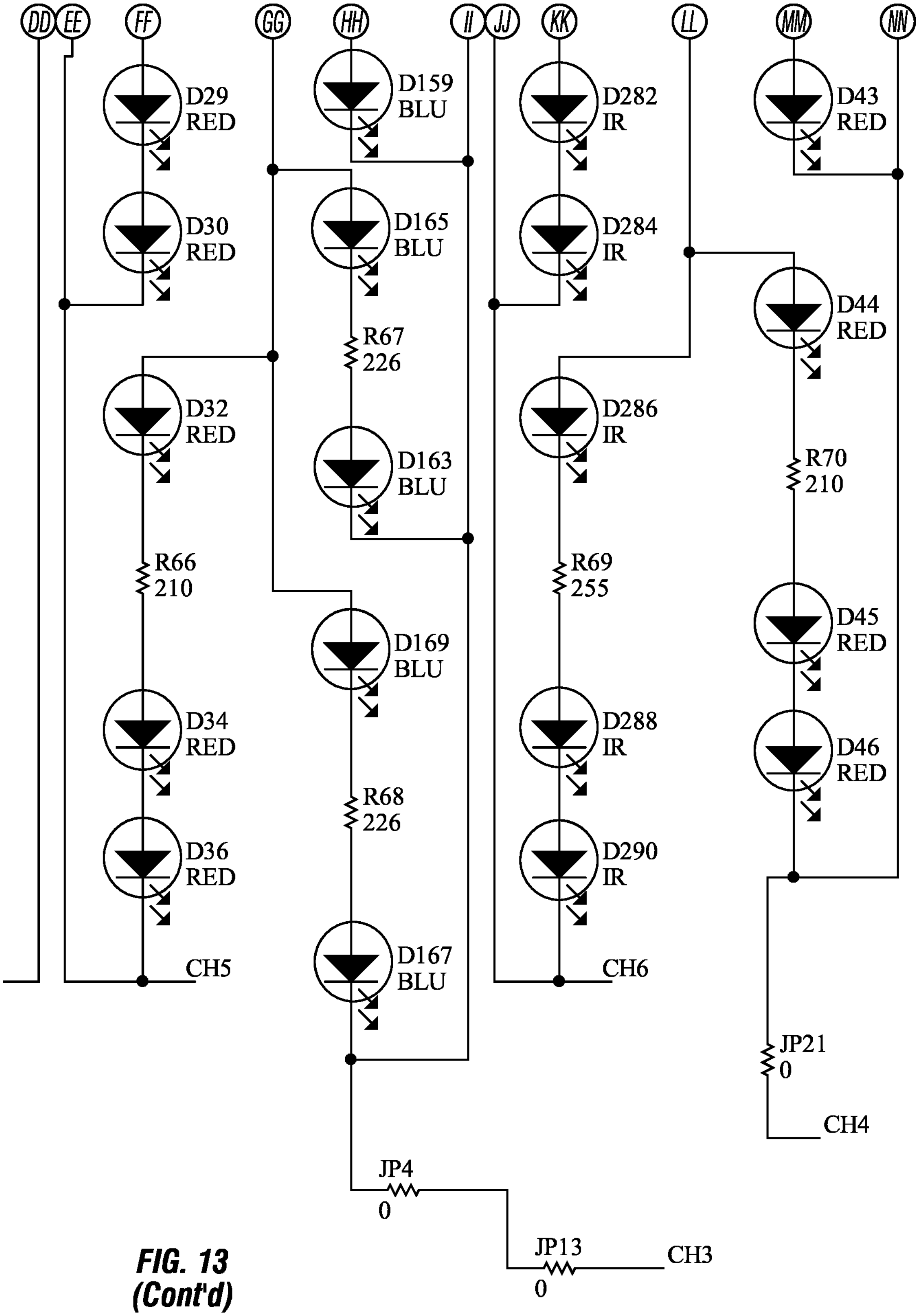
Figure 13:
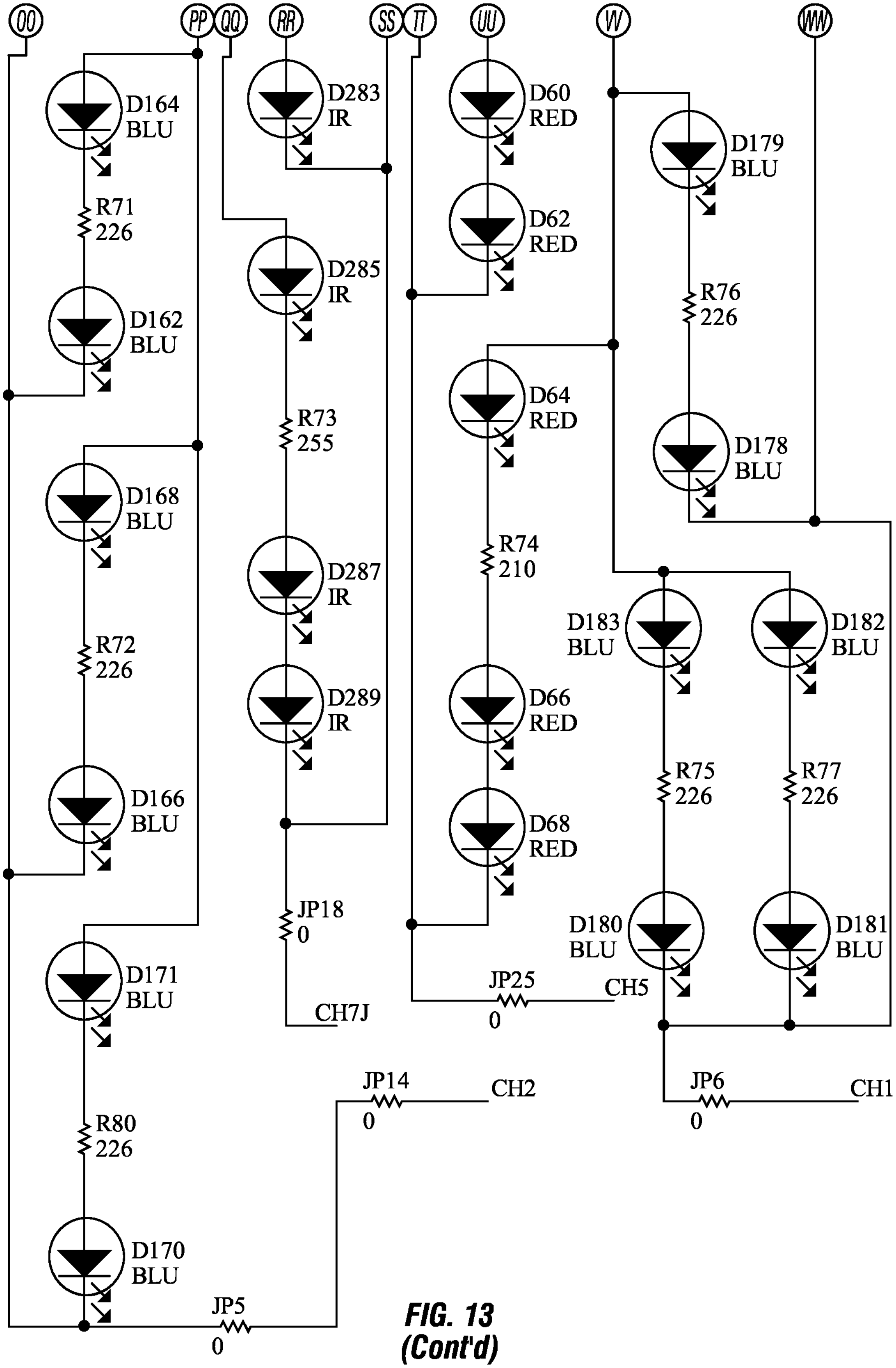
Figure 13:
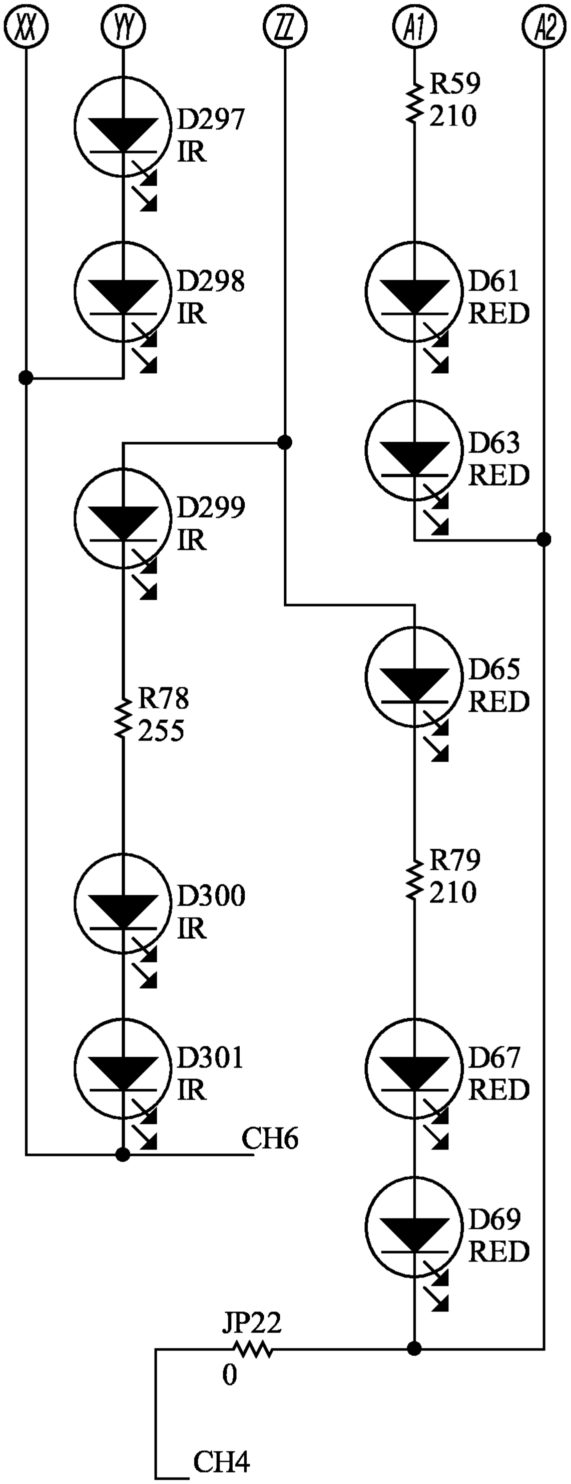
Figure 14:
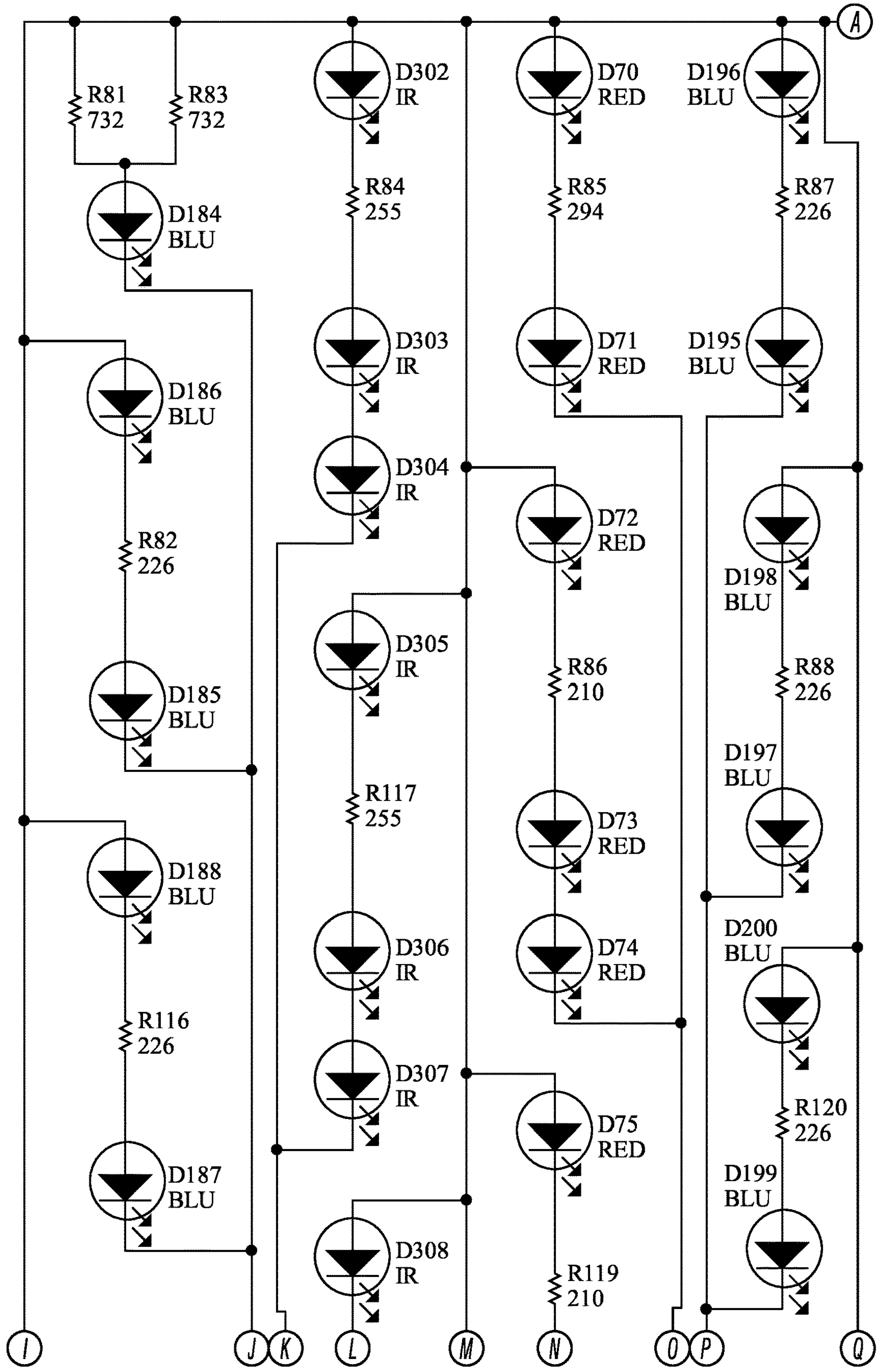
FIG. 14 is a schematic of a second portion of the LED array useable in the shapeable light therapy device of FIG. 1.
Figure 14:
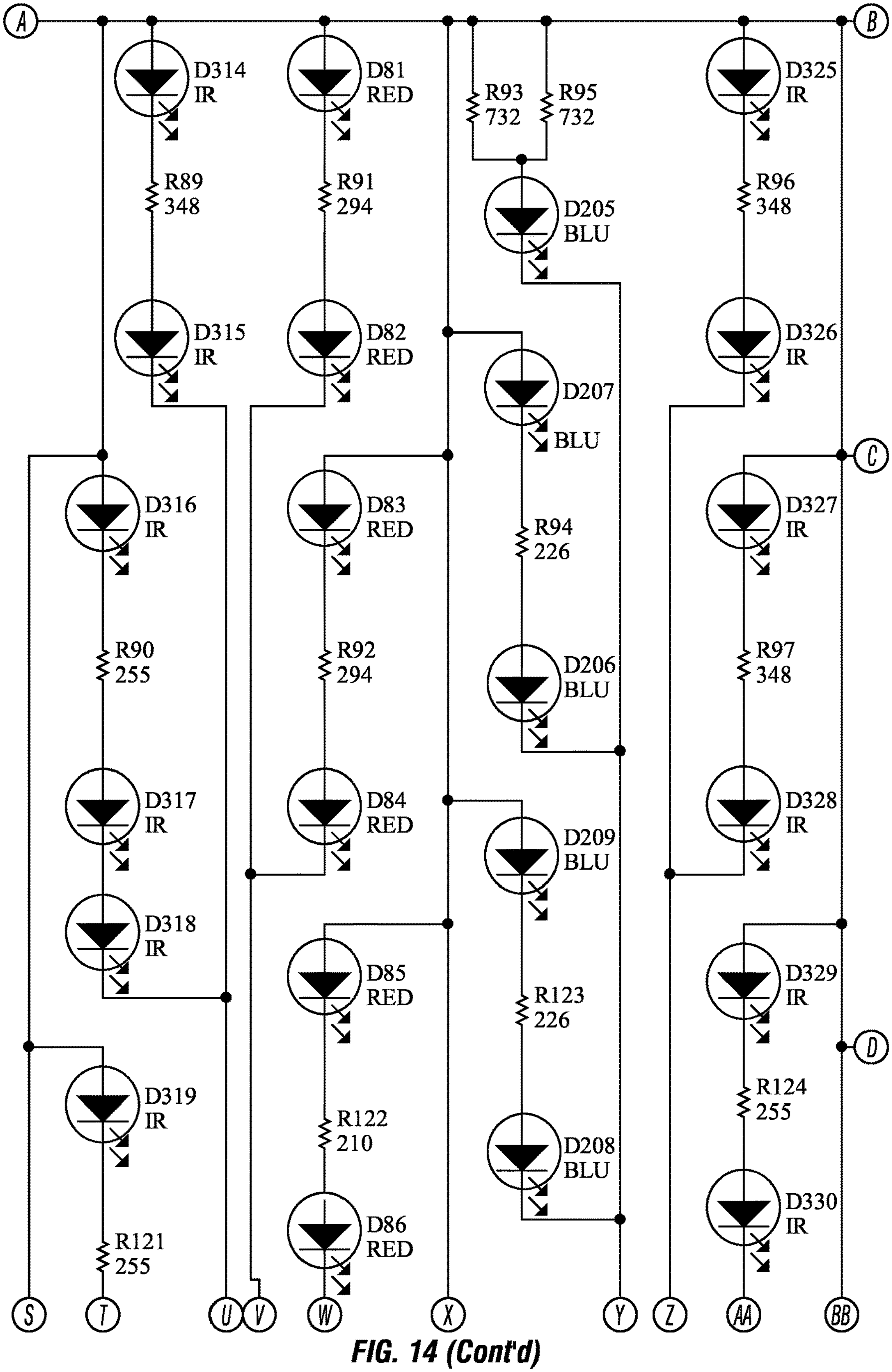
Figure 14:
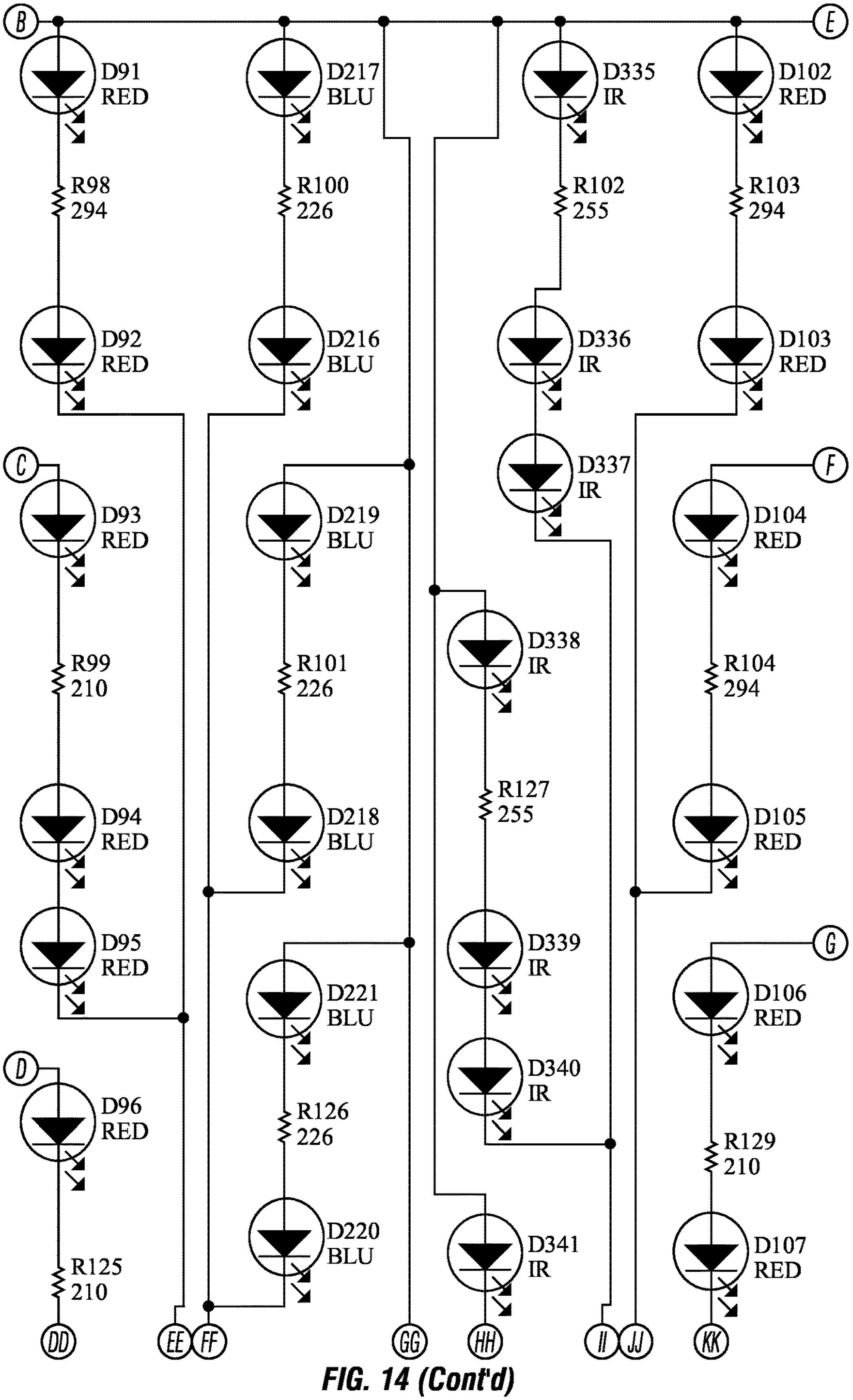
Figure 14:
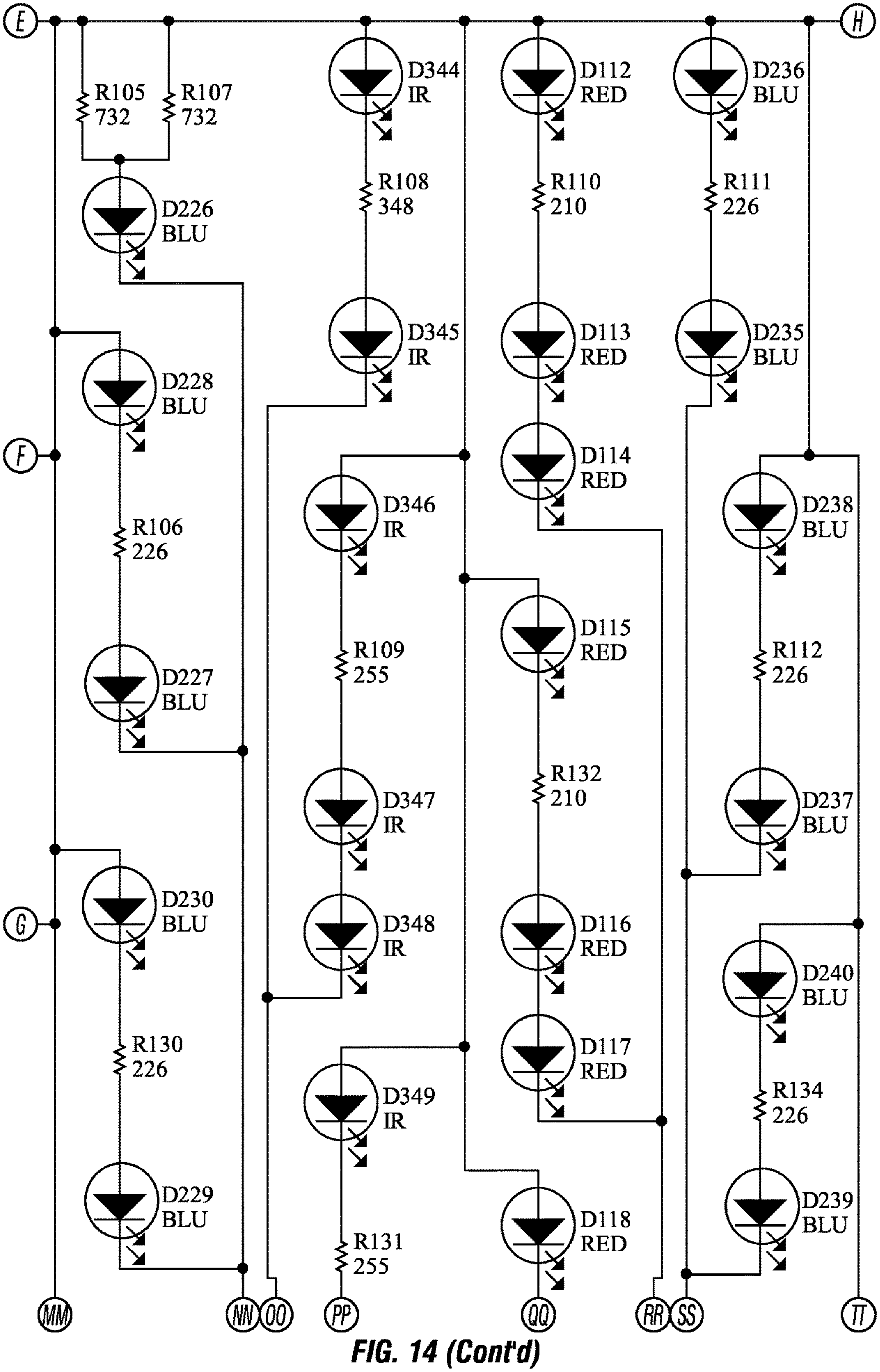
Figure 14:
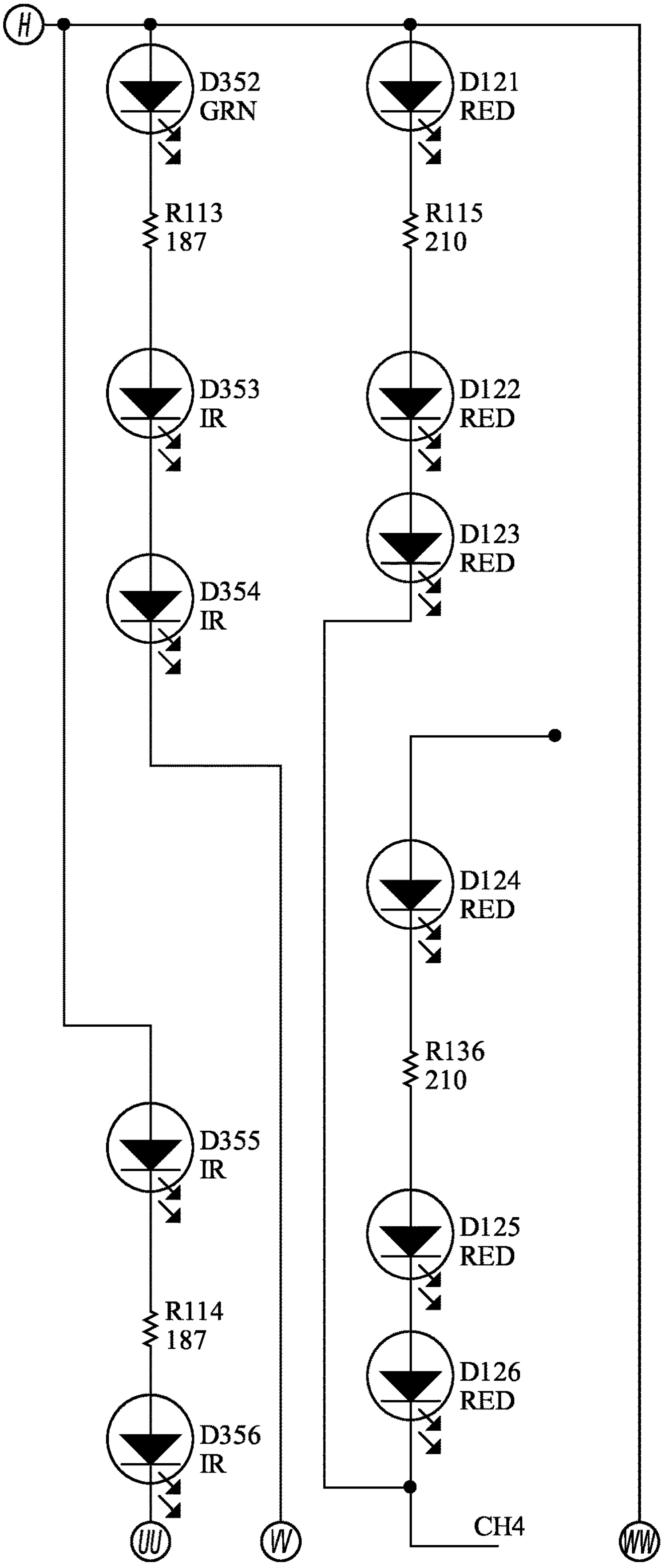
Figure 14:
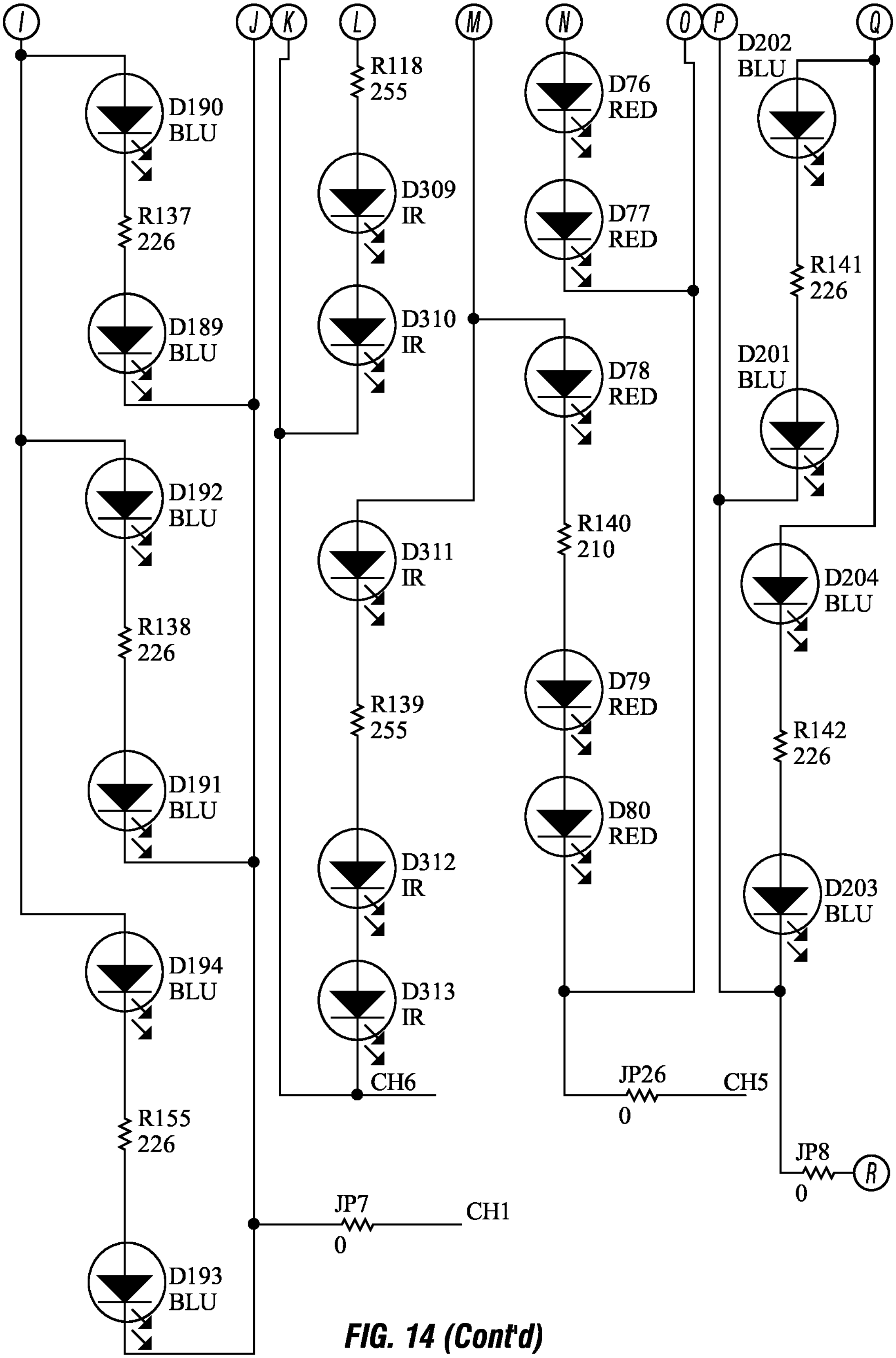
Figure 14:
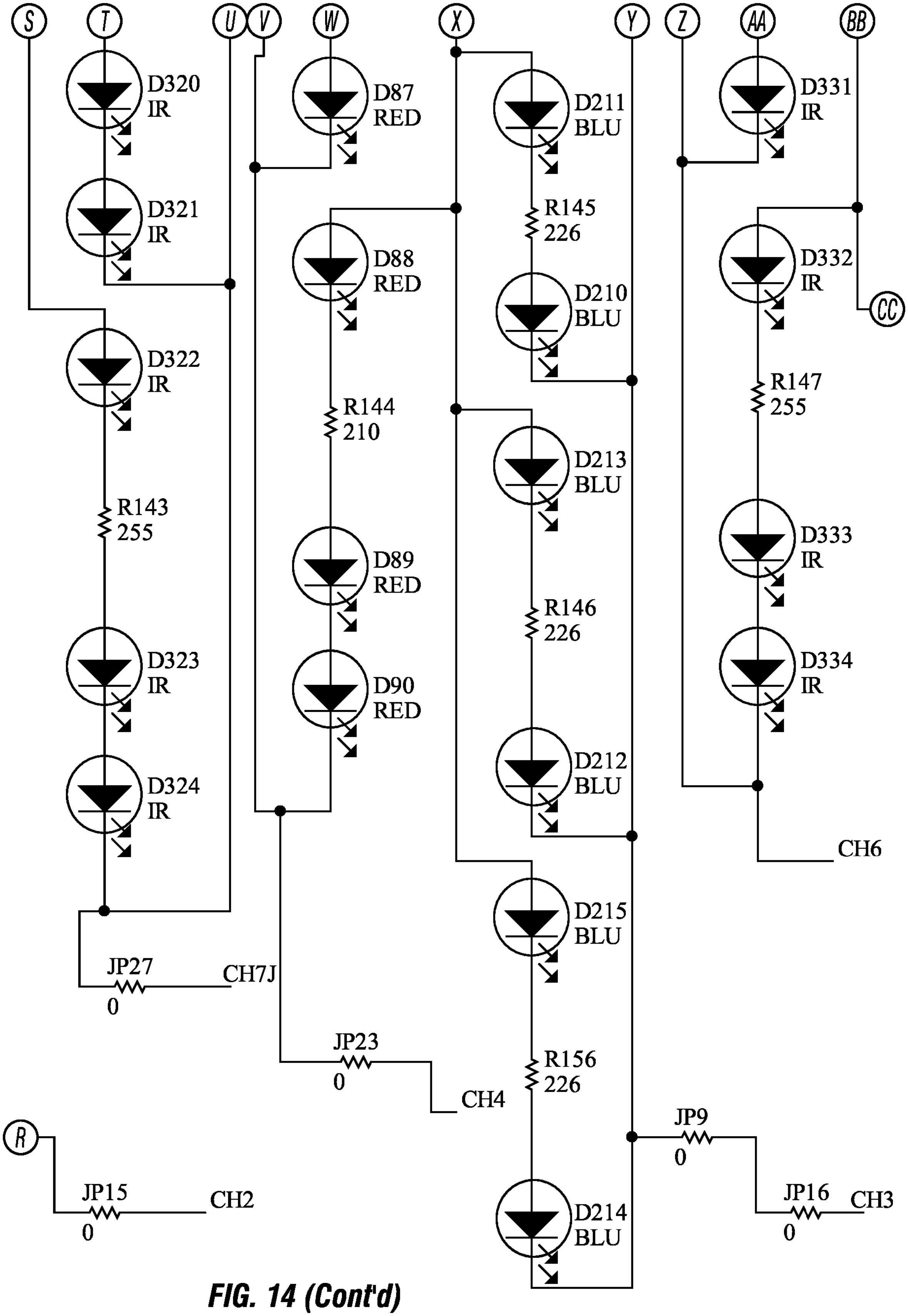
Figure 14:
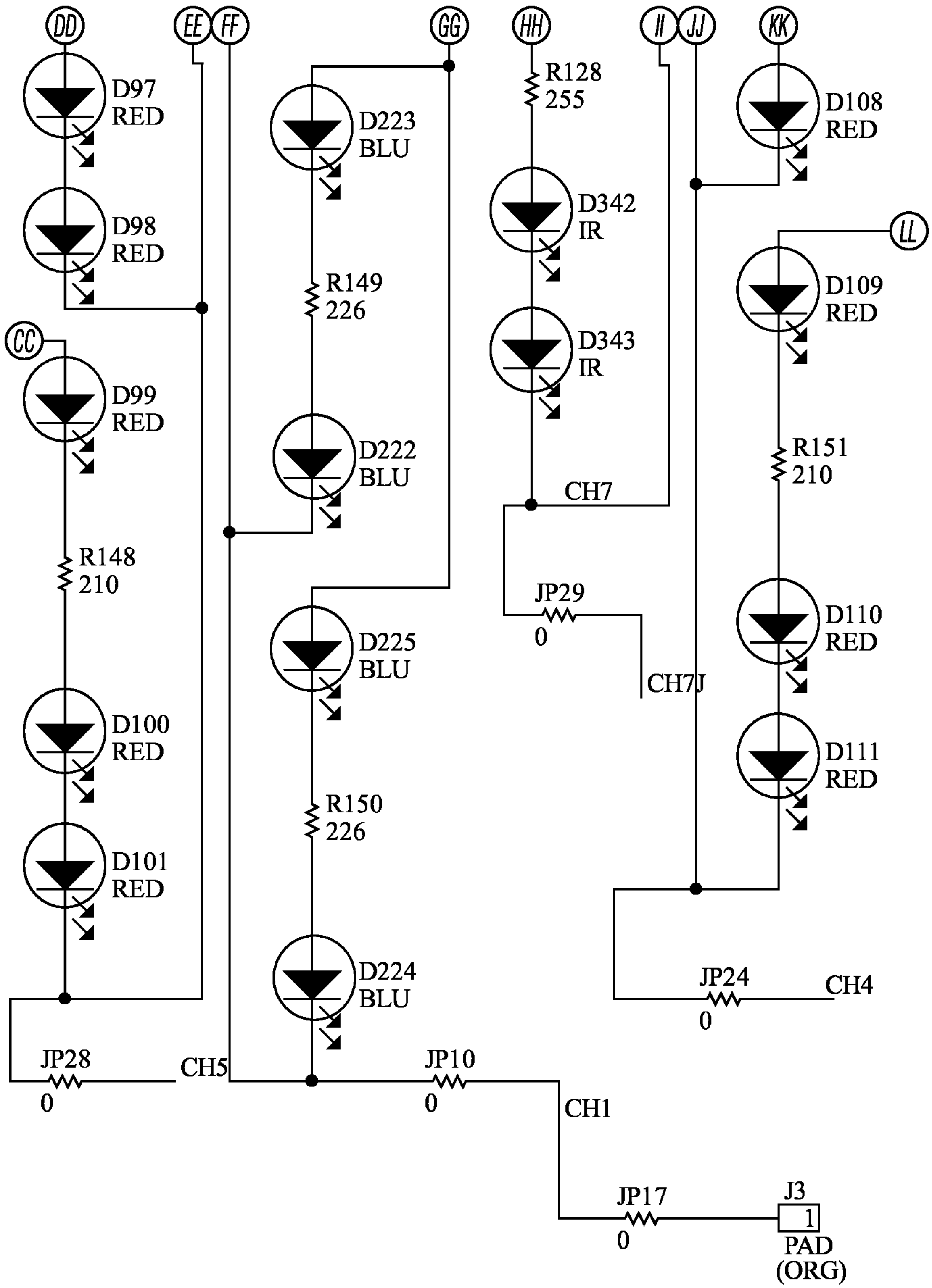
Figure 14:
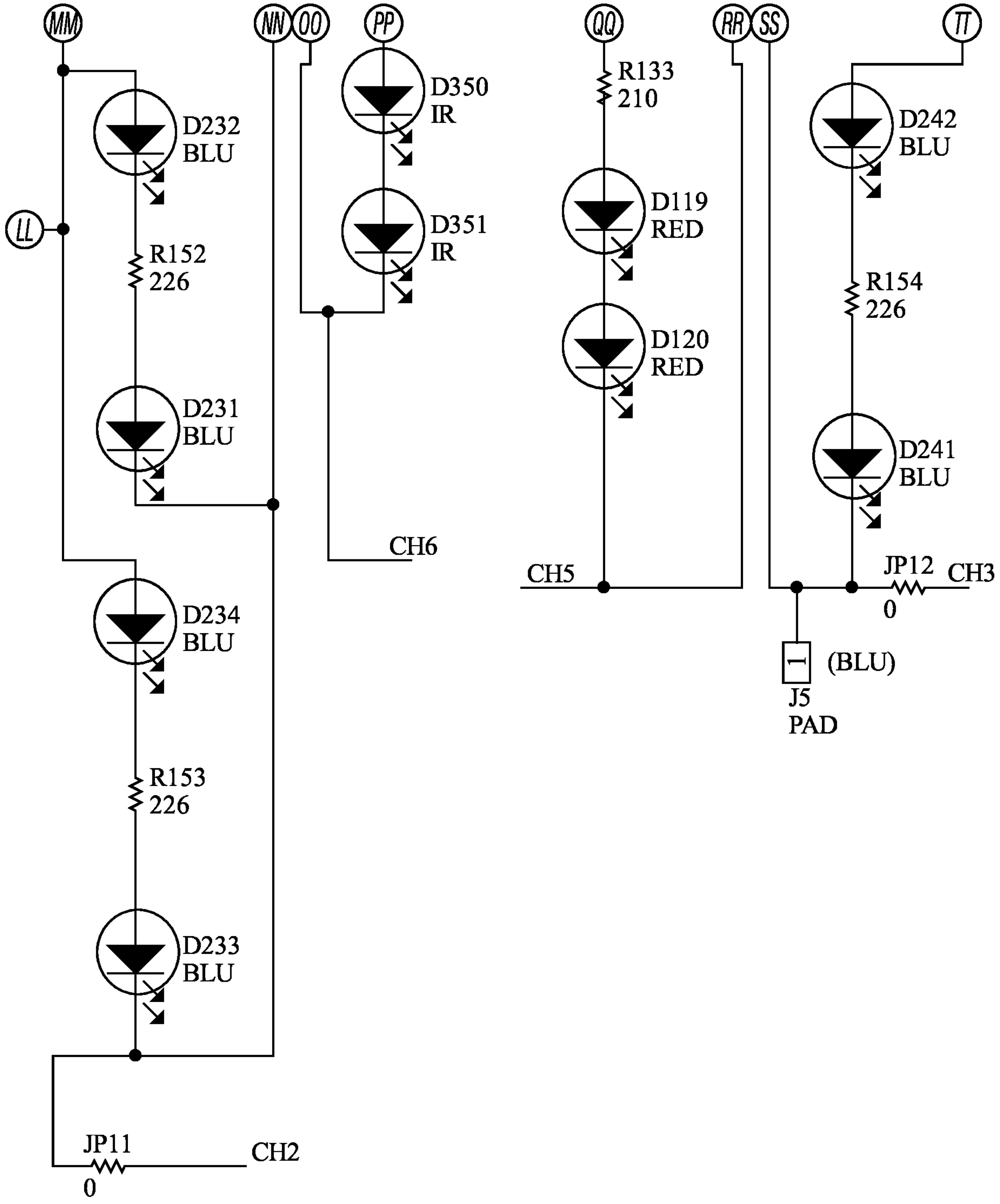
Figure 14:
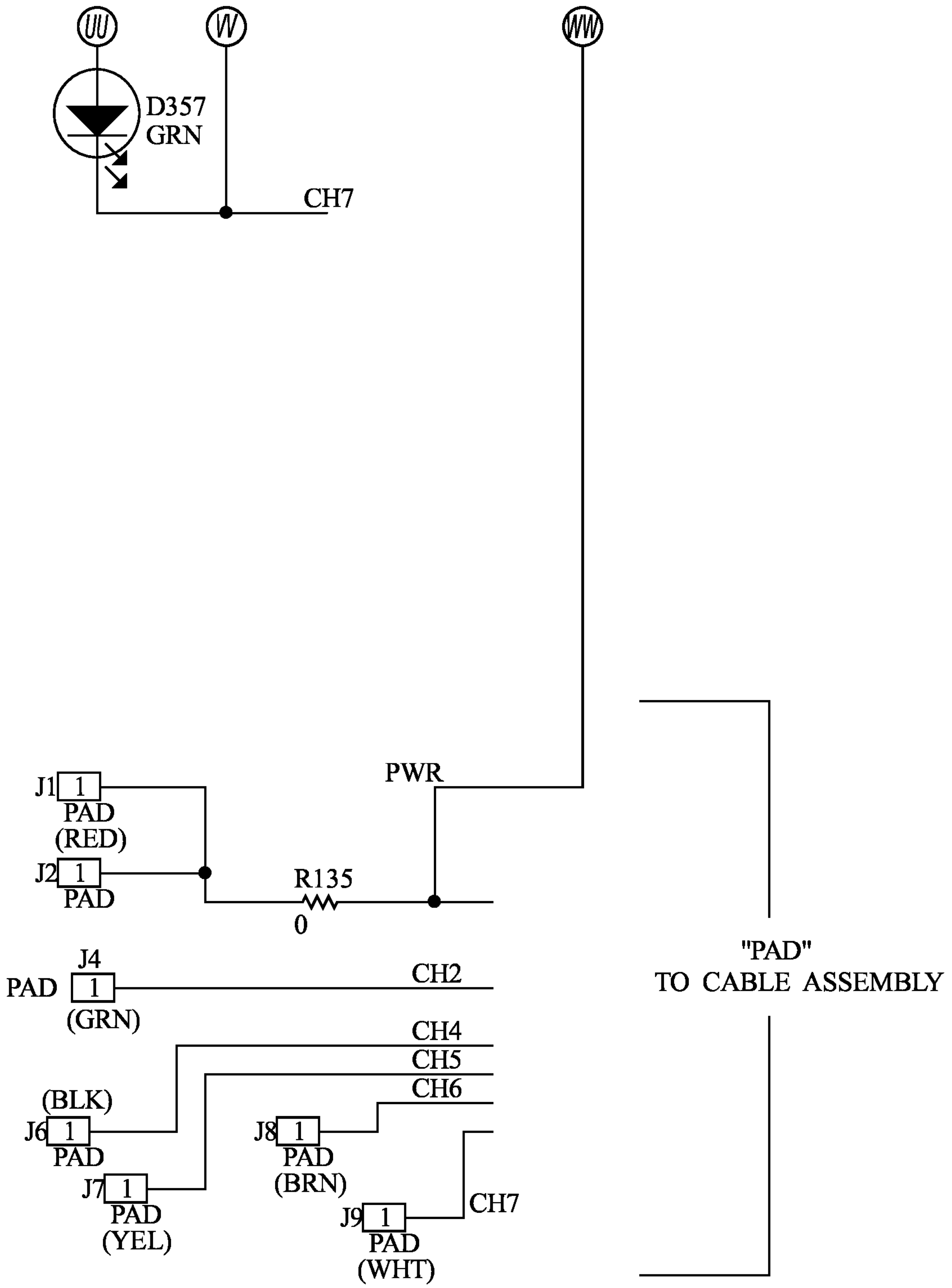
Figure 15:
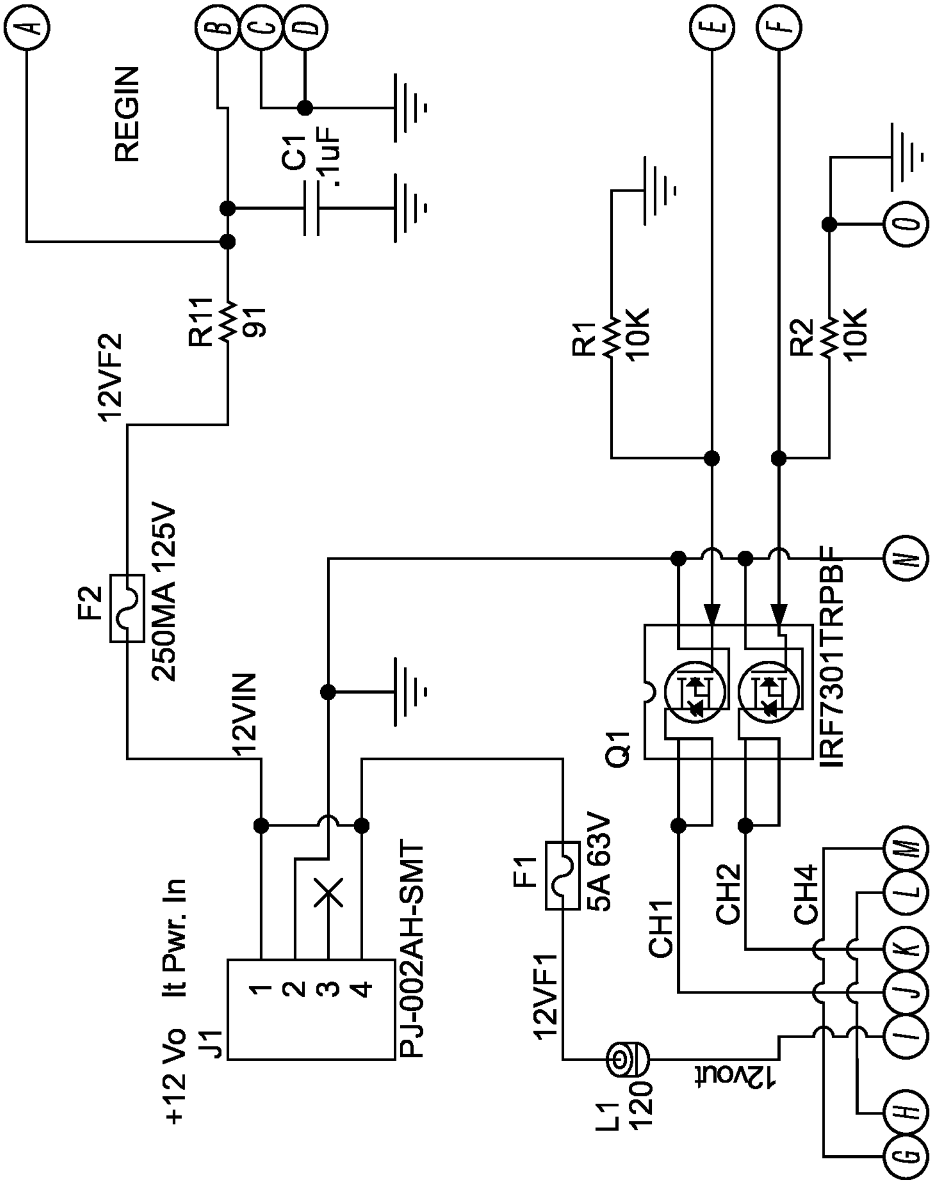
FIG. 15 is a schematic of a controller circuit board useable in the system of FIG. 1.
Figure 15:
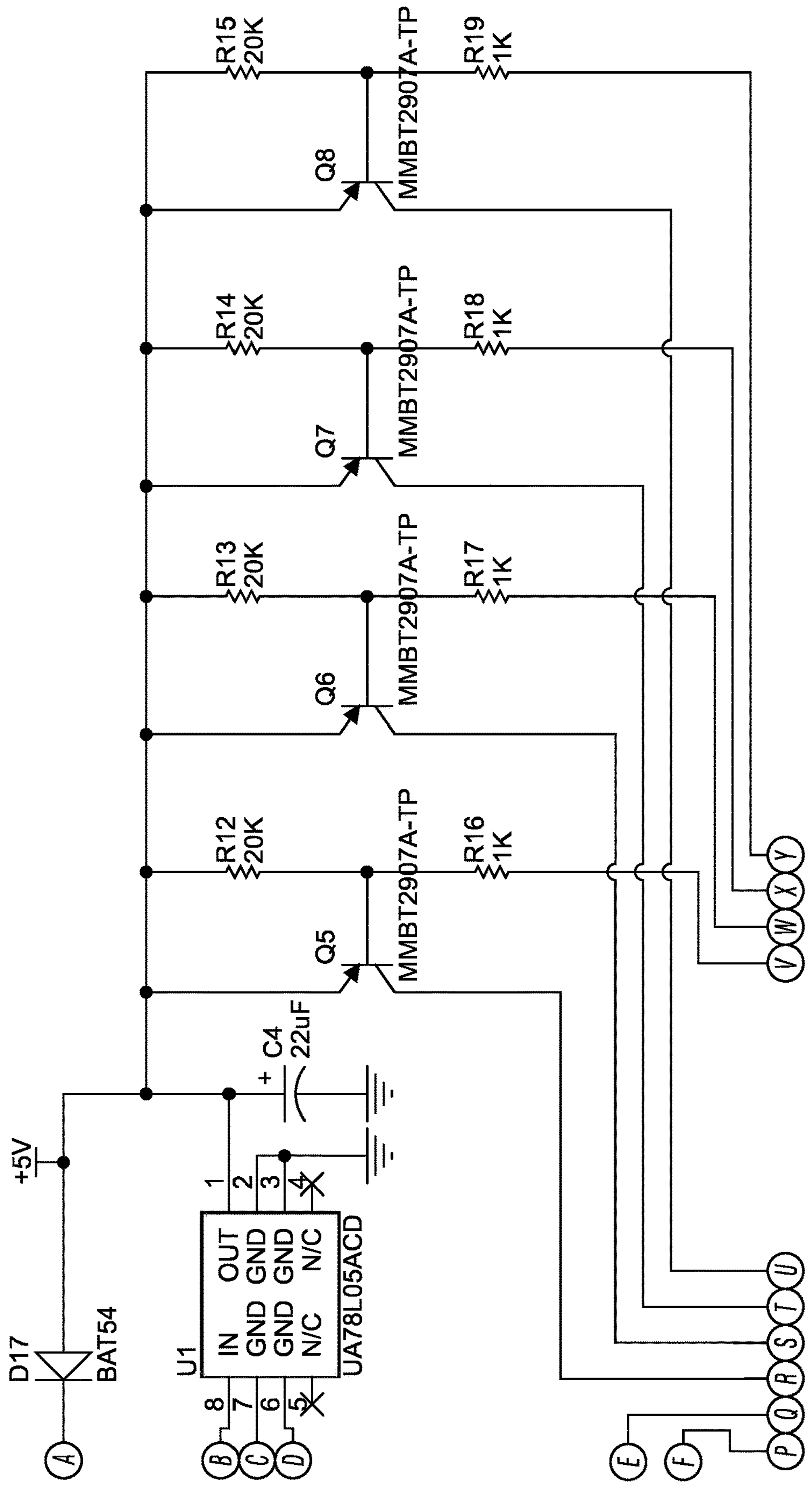
Figure 15:
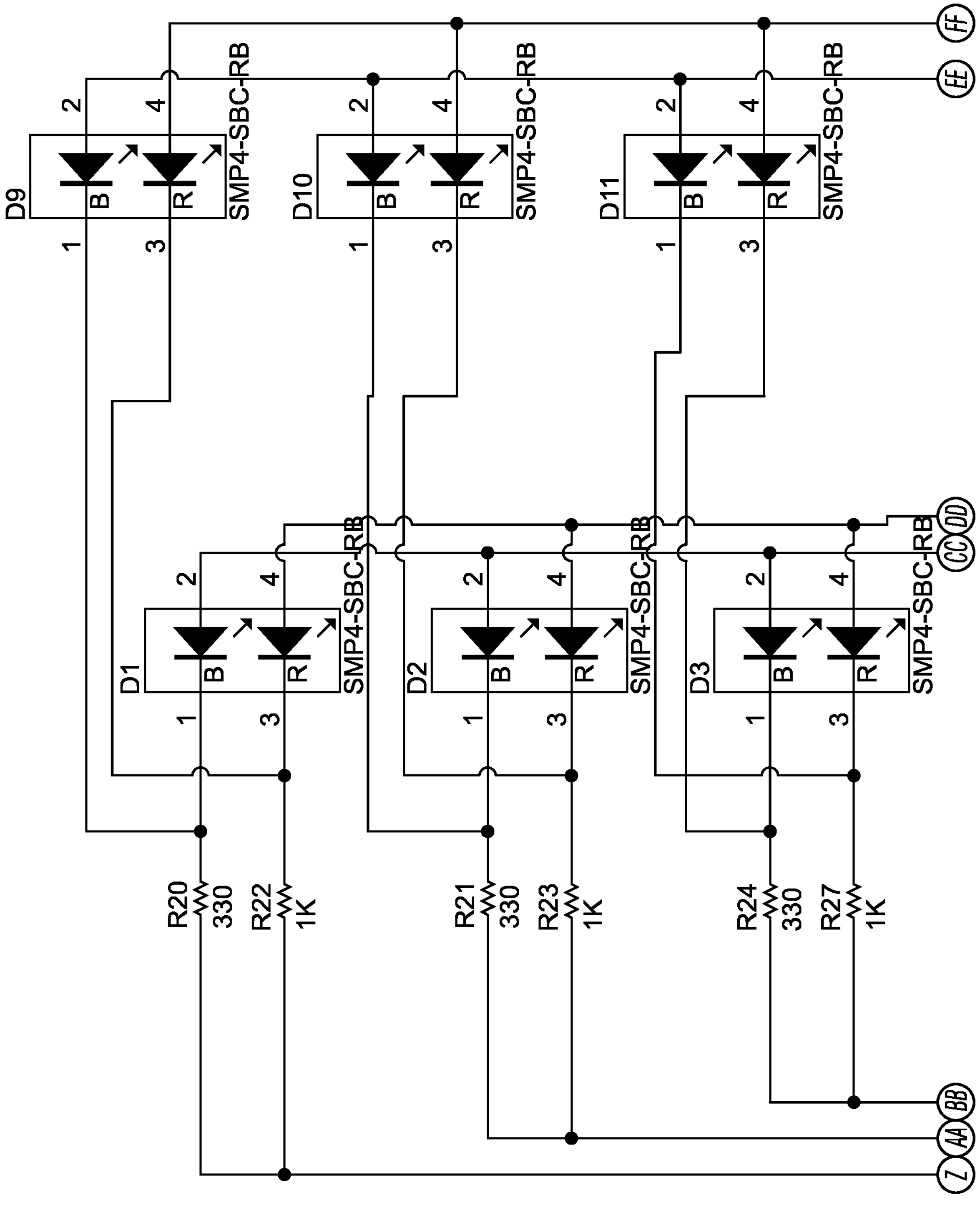
Figure 15:
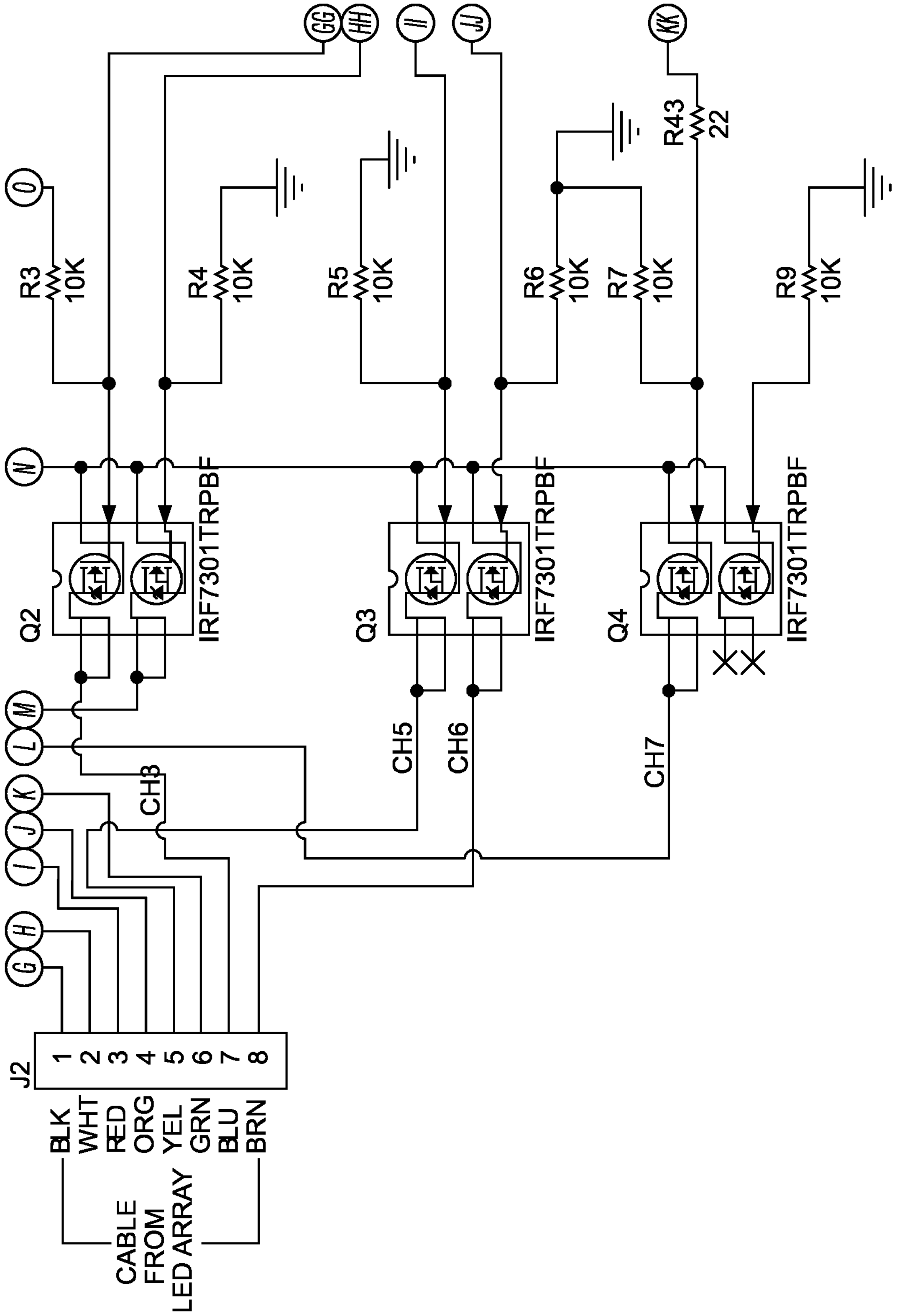
Figure 15:
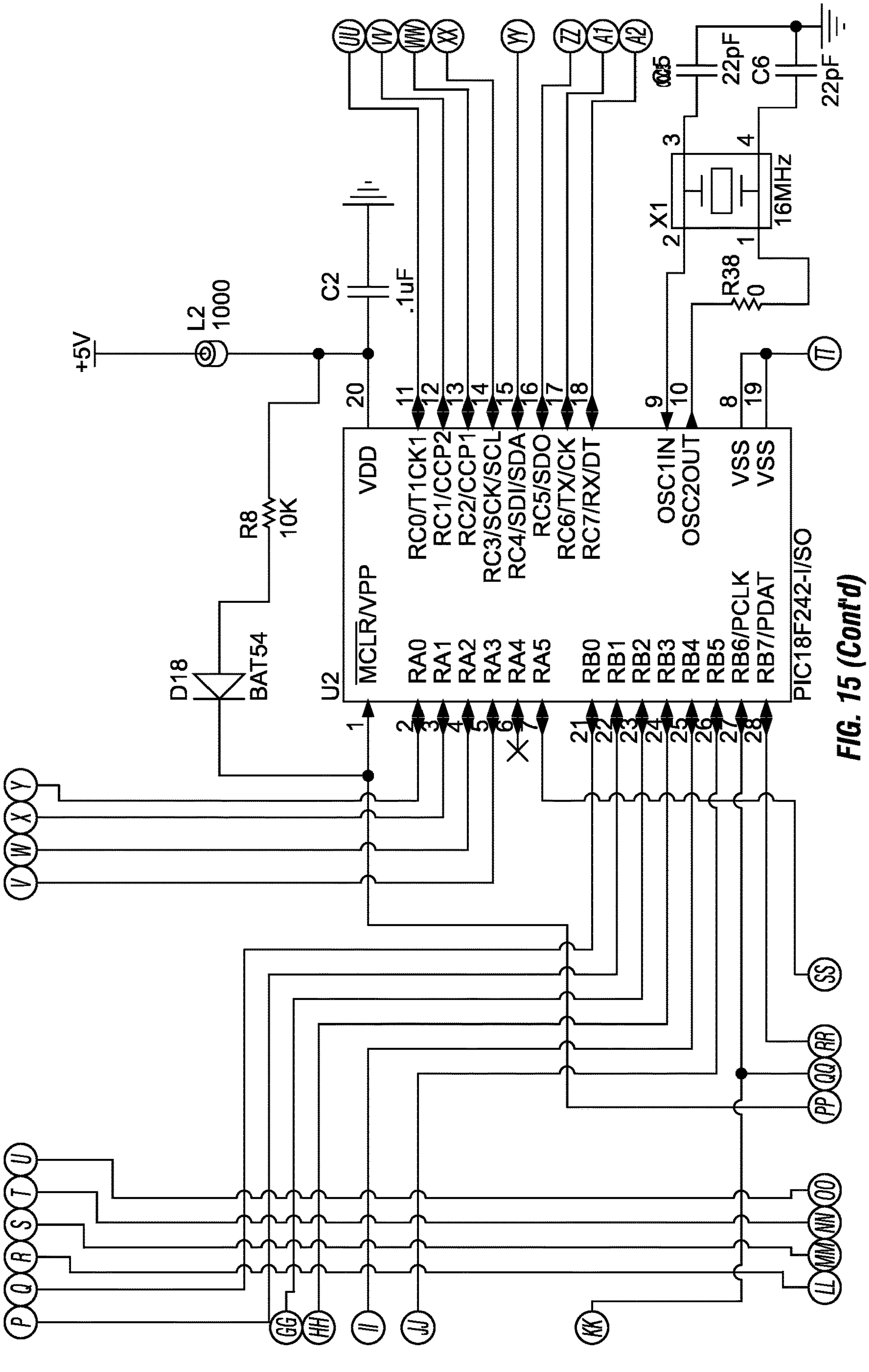
Figure 15:
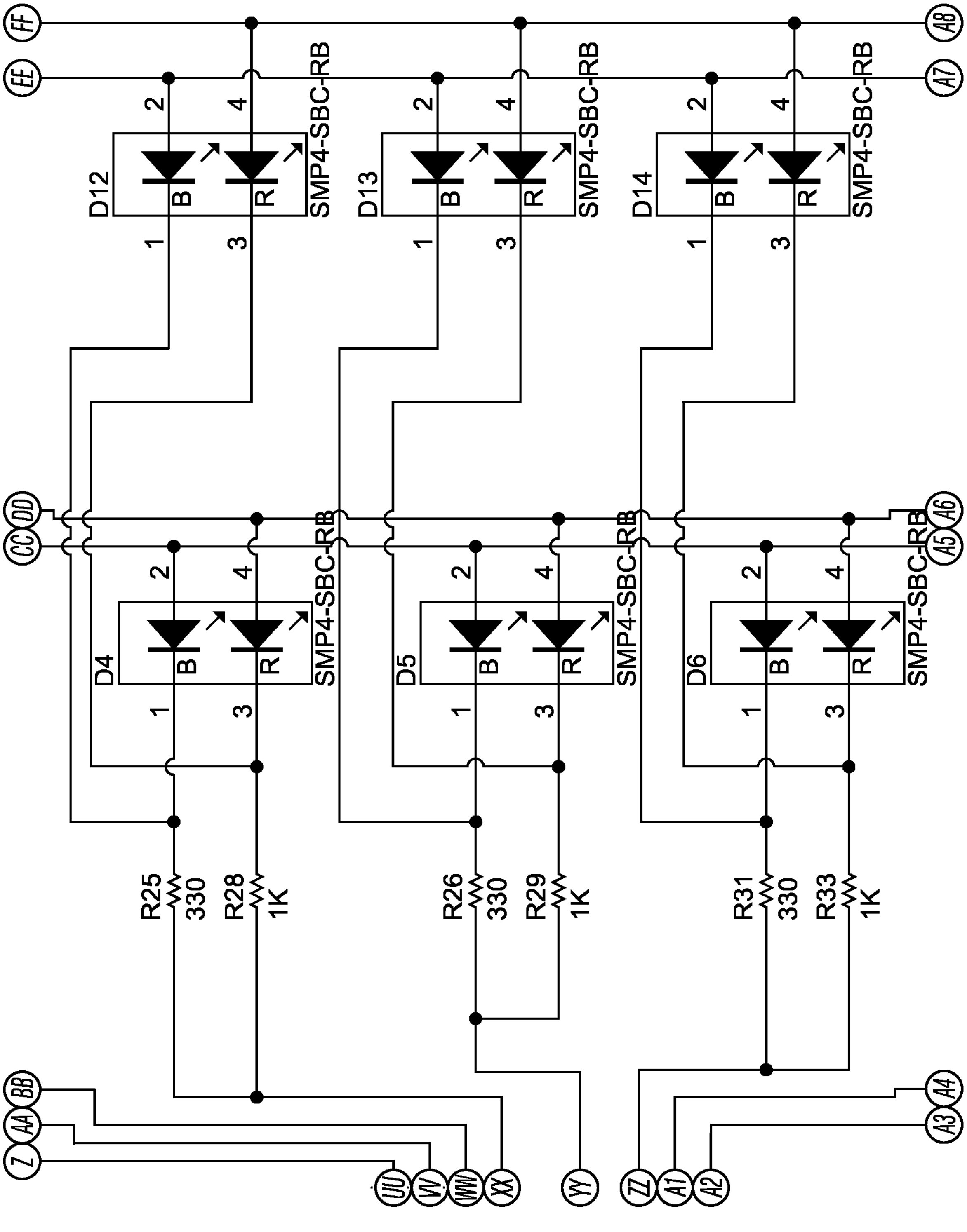
Figure 15:
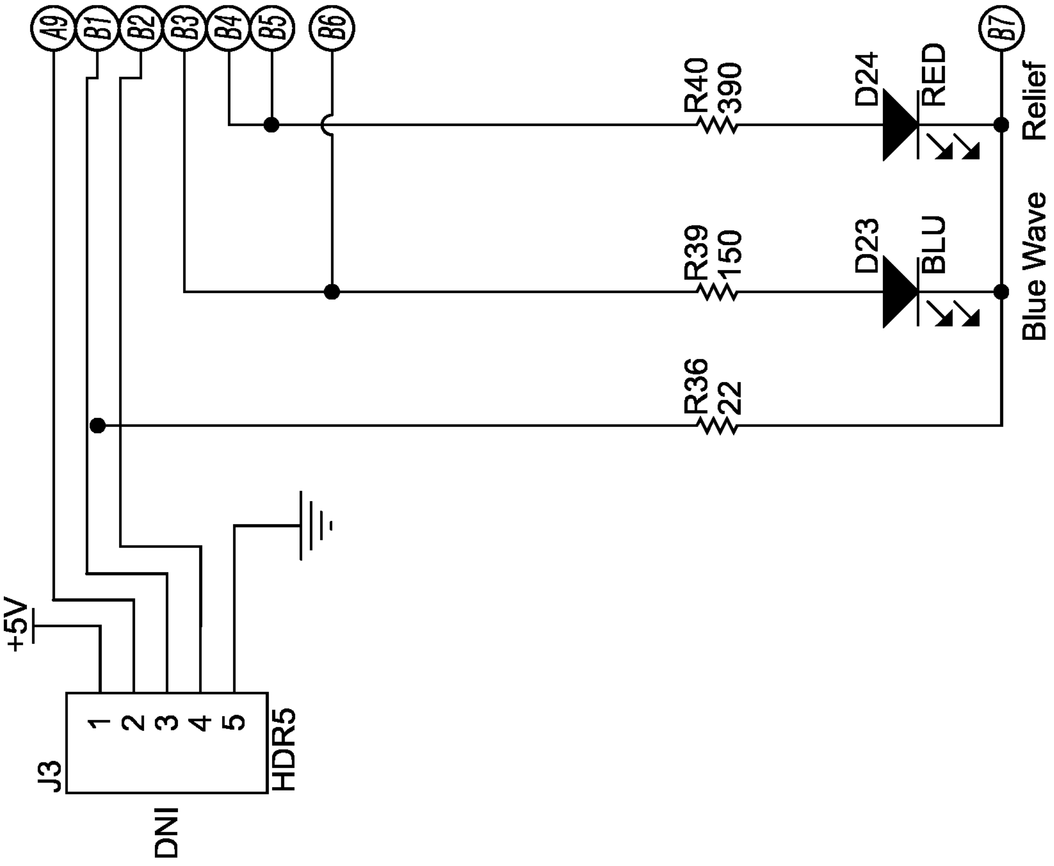
Figure 15:
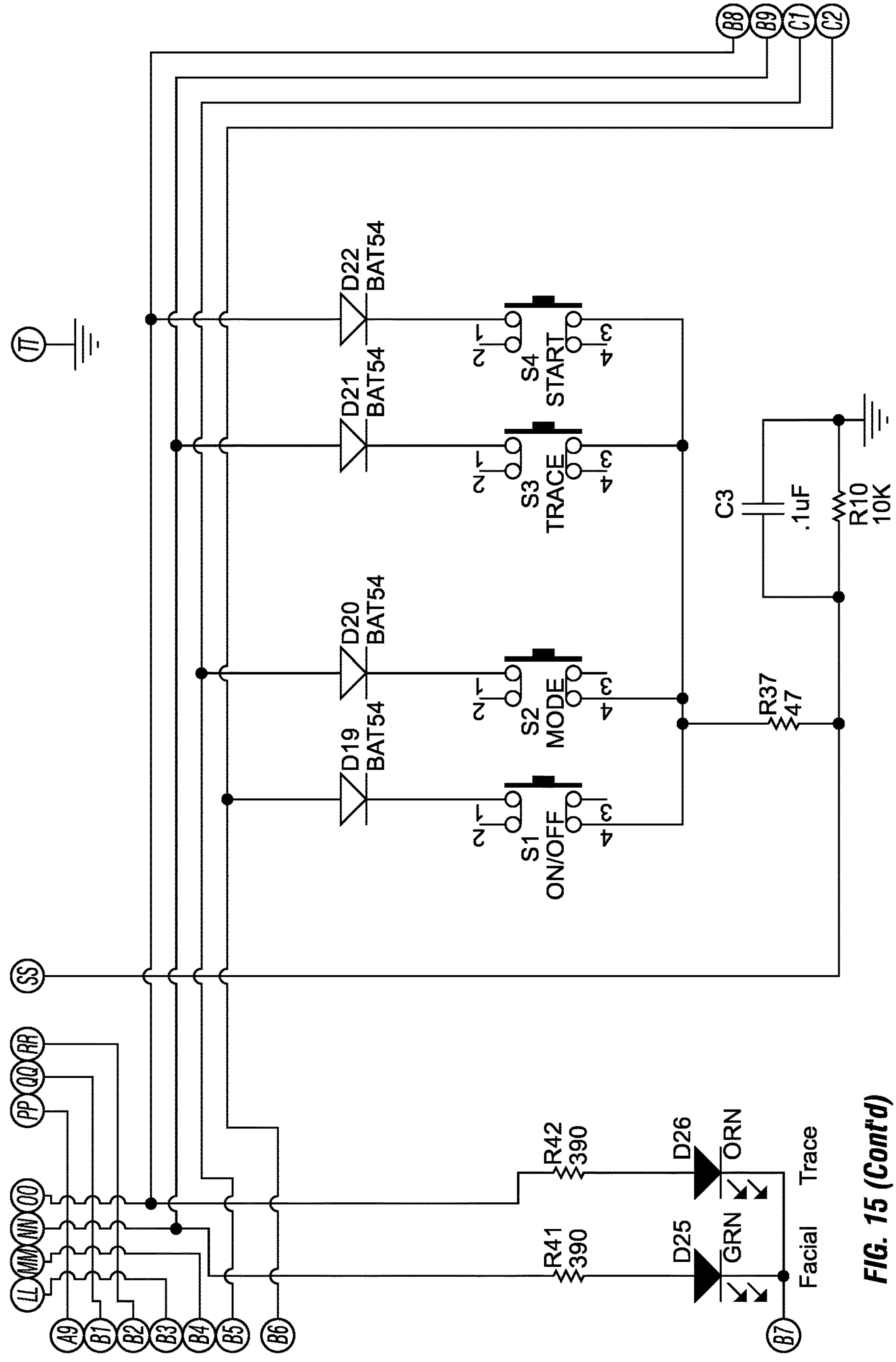
Figure 15:
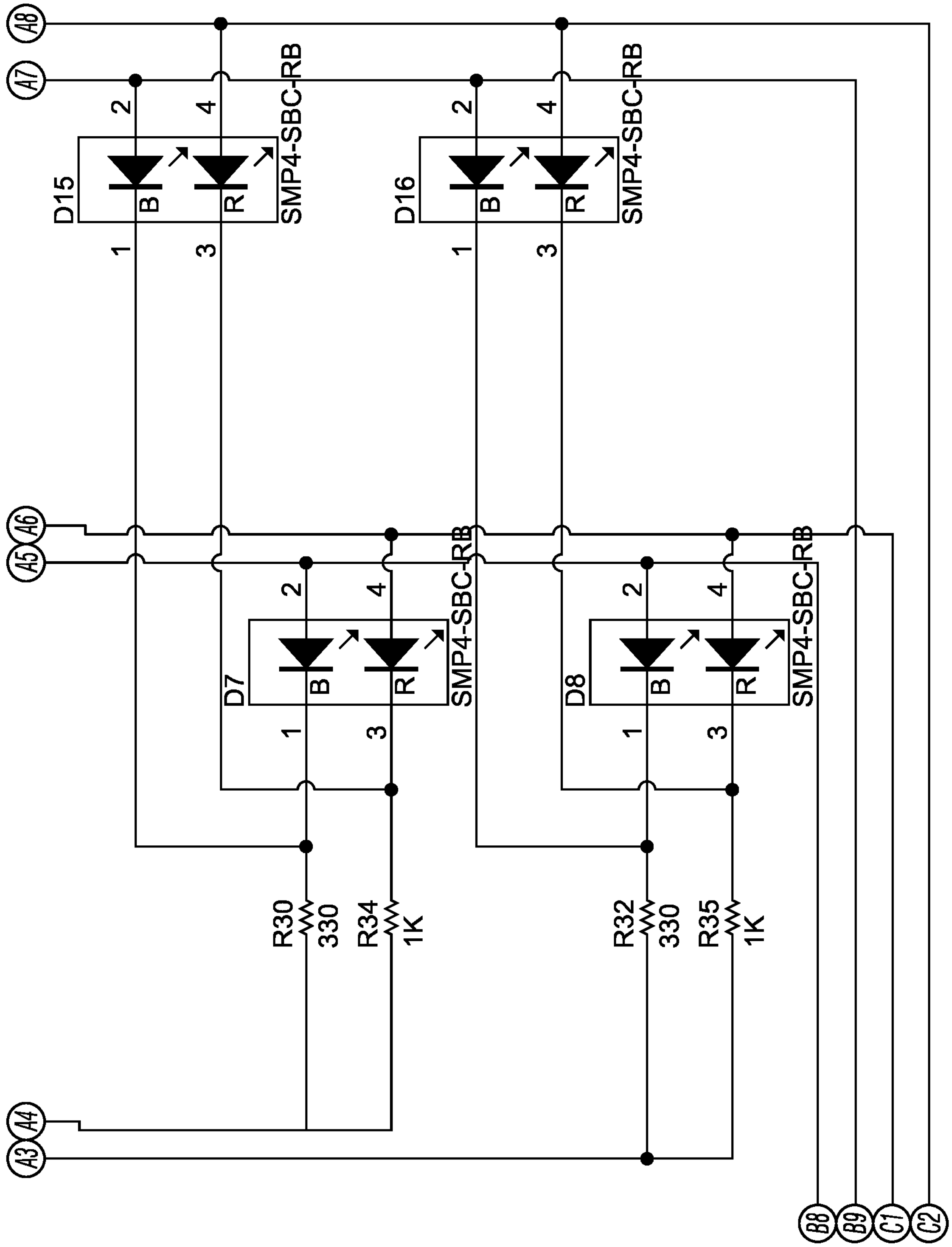
Figure 16:
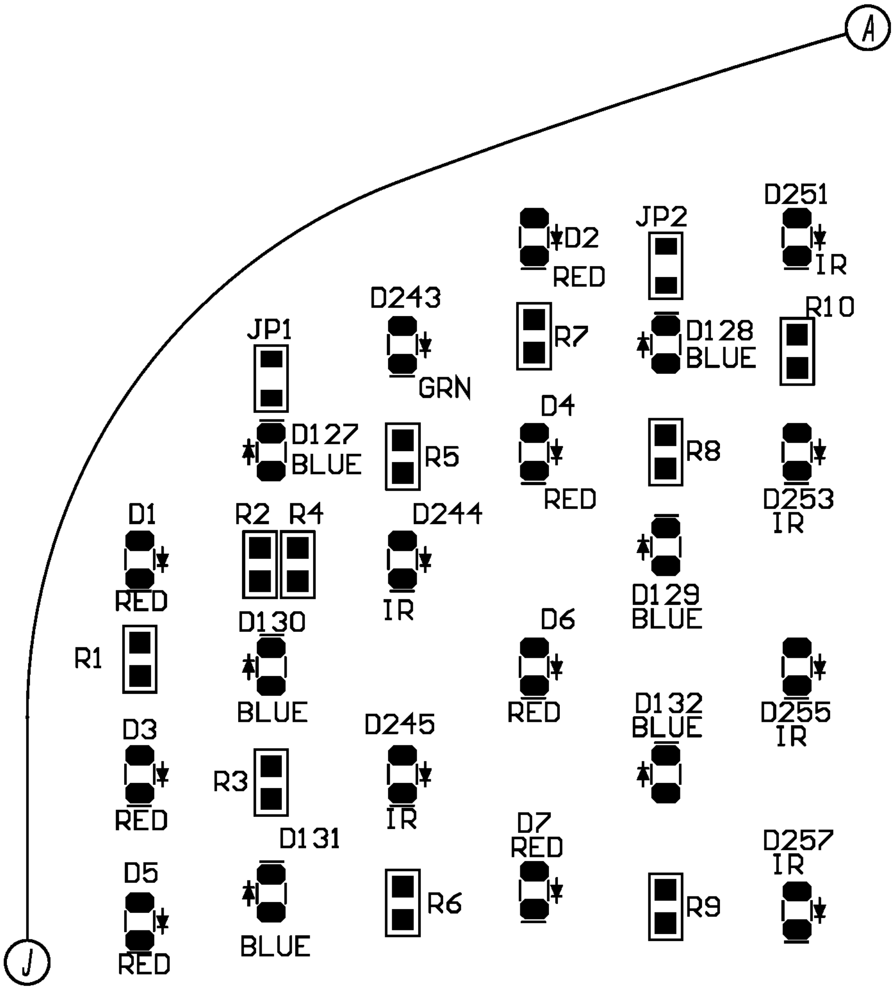
FIG. 16 is a primary (front) side view of a PCBA of an LED array useable in the shapeable light therapy device of FIG. 1
Figure 16:
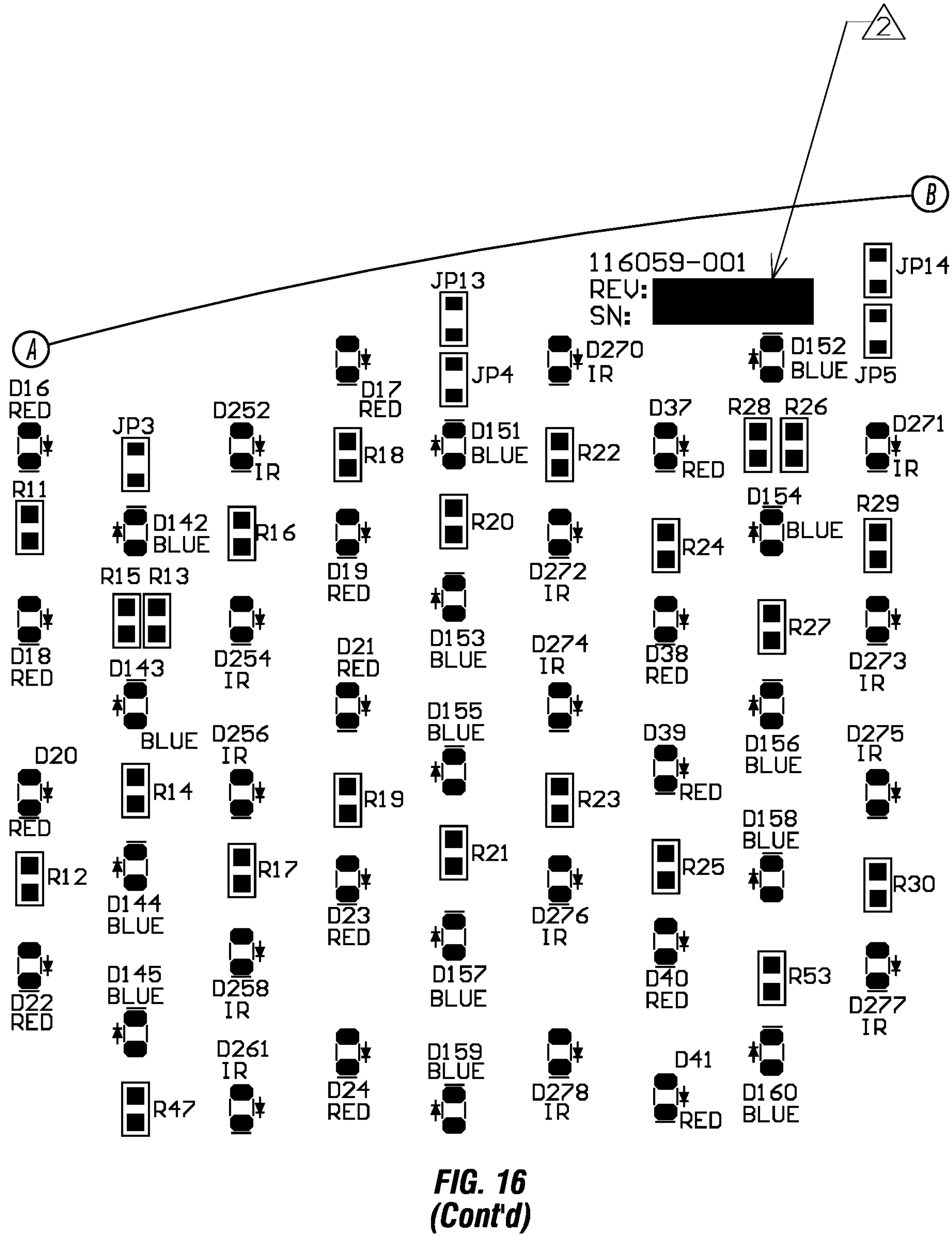
Figure 16:
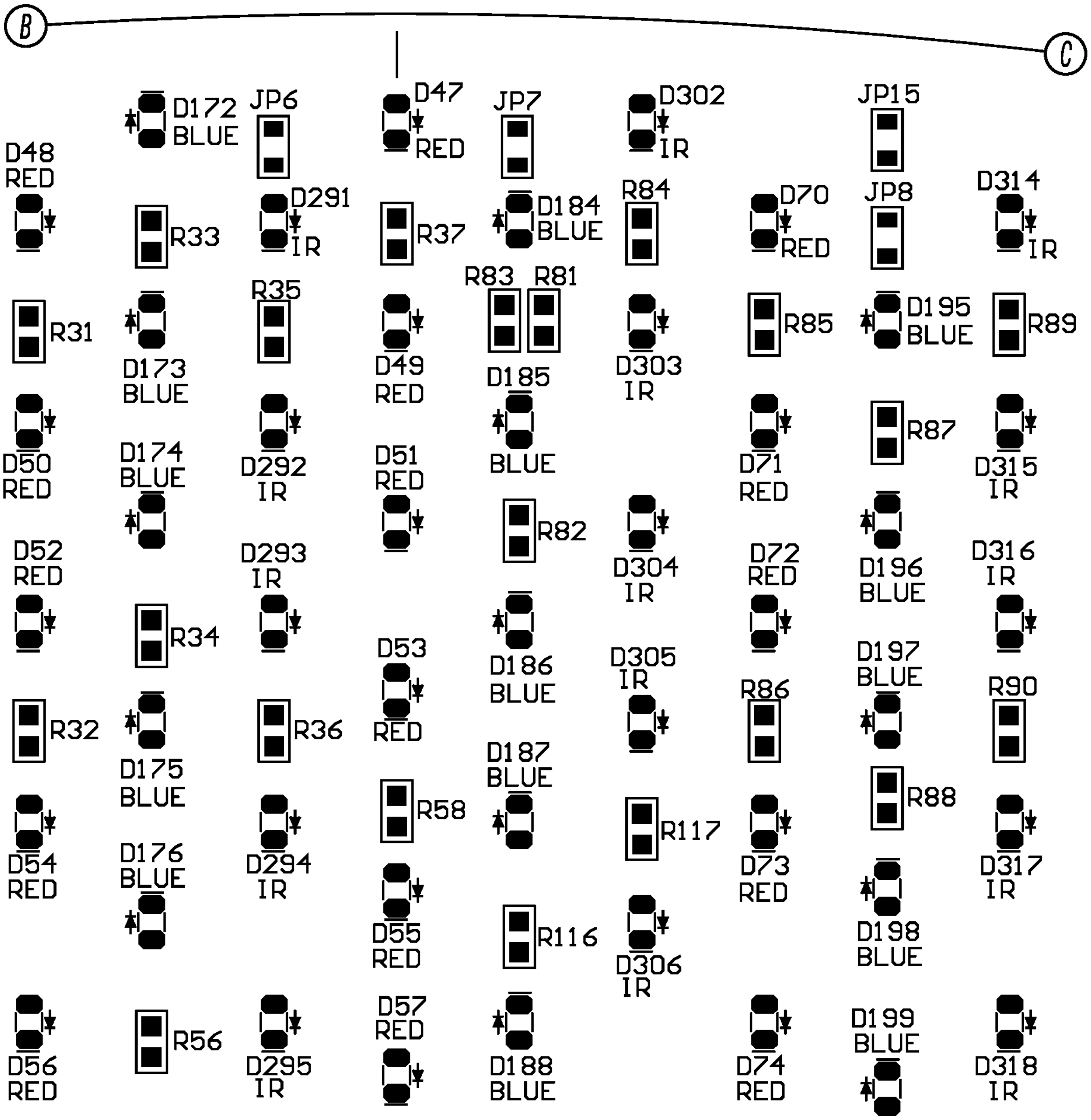
Figure 16:
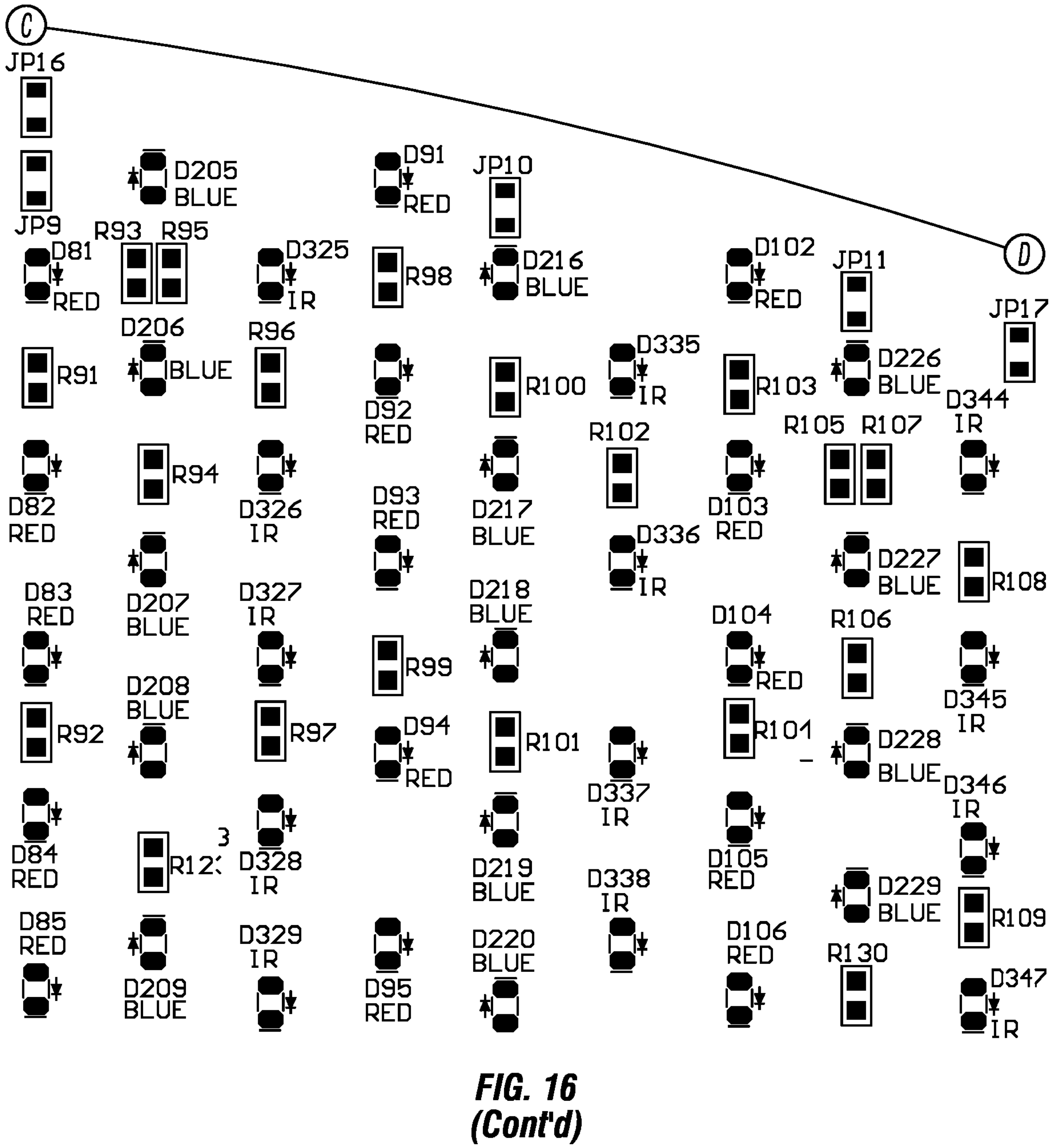
Figure 16:
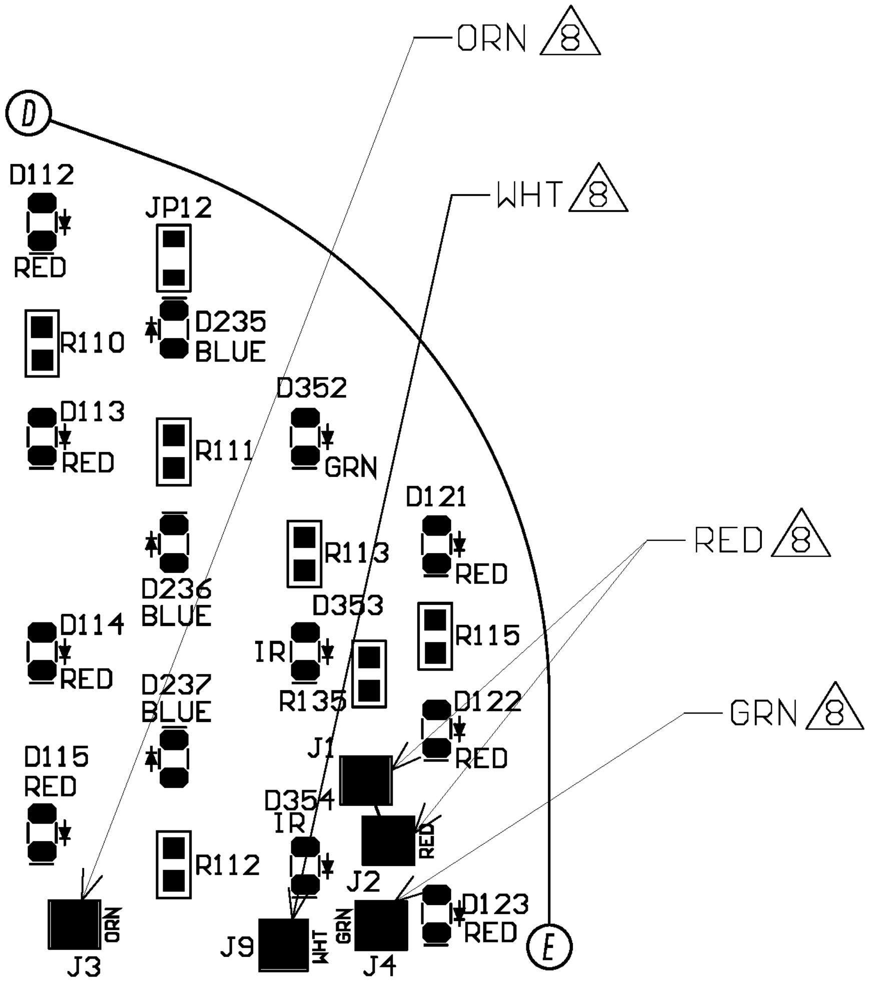
Figure 16:
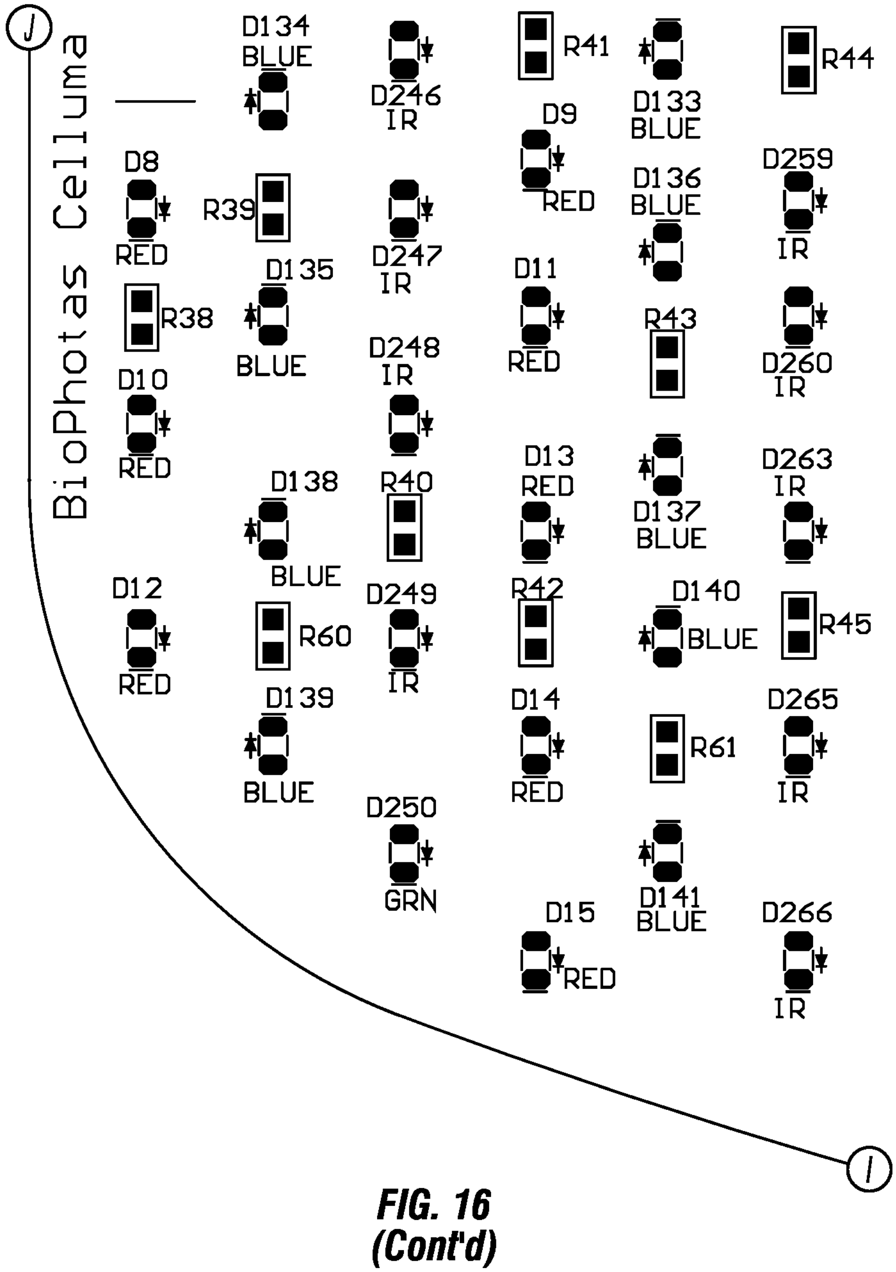
Figure 16:
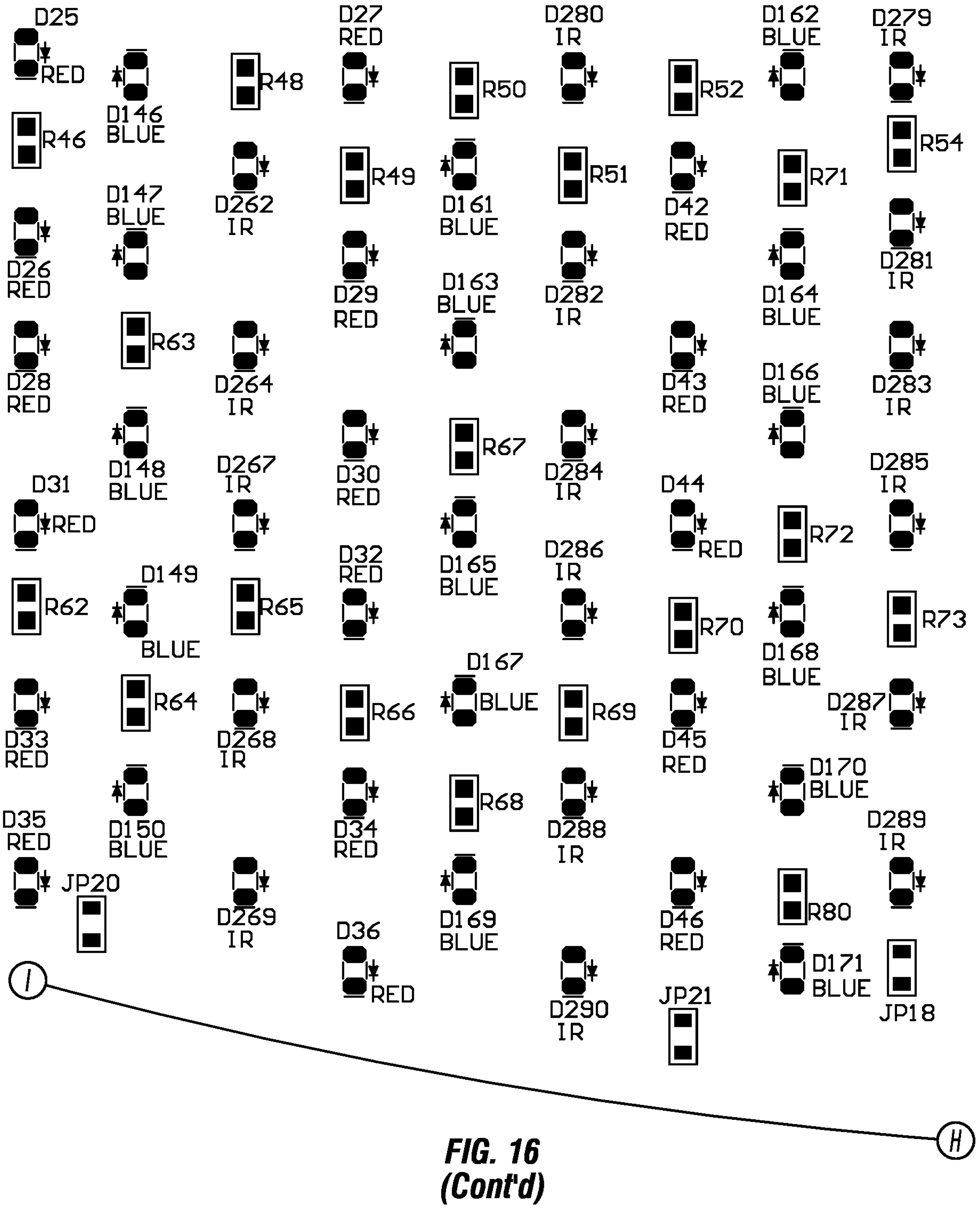
Figure 16:
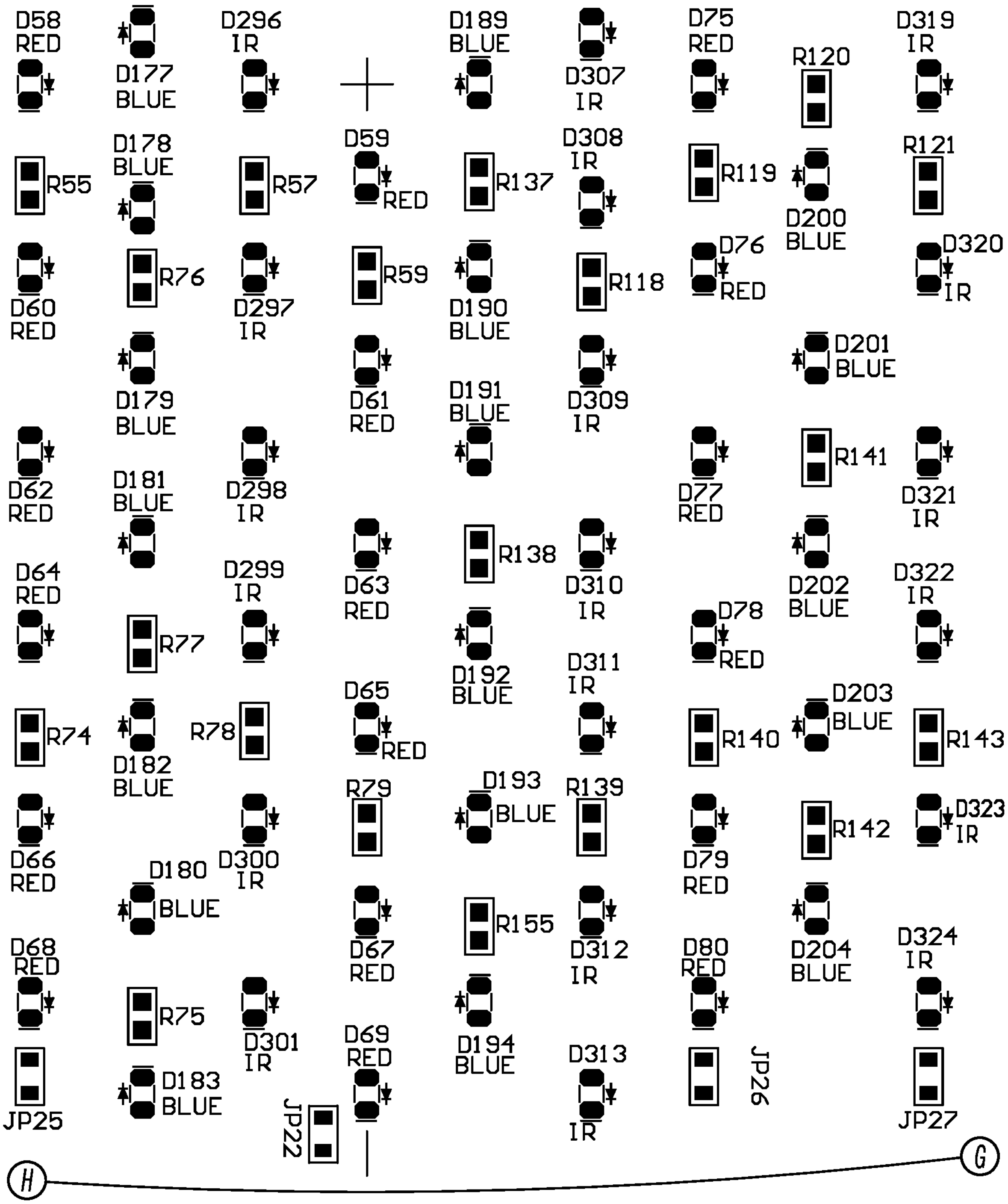
Figure 16:
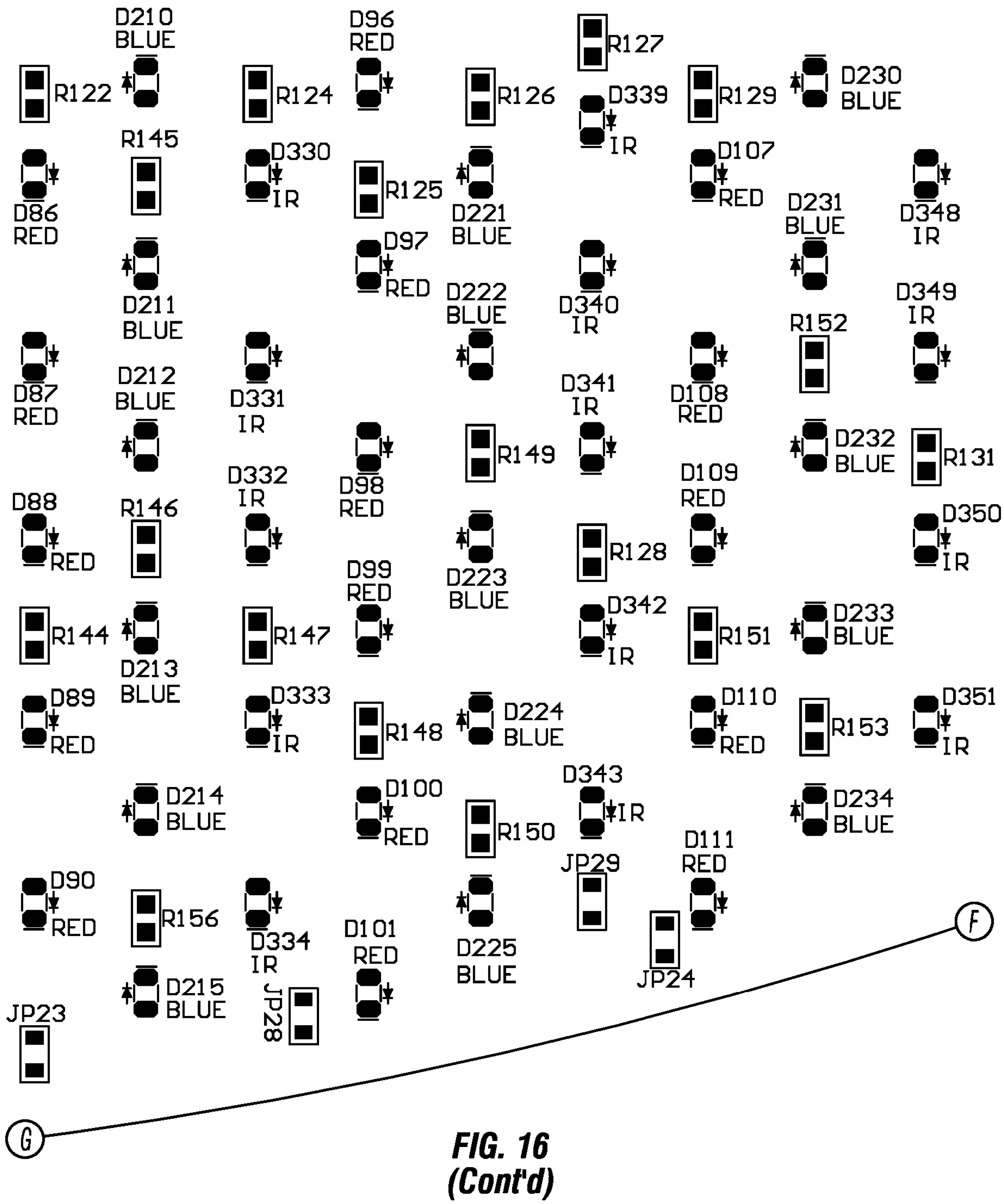
Figure 16:
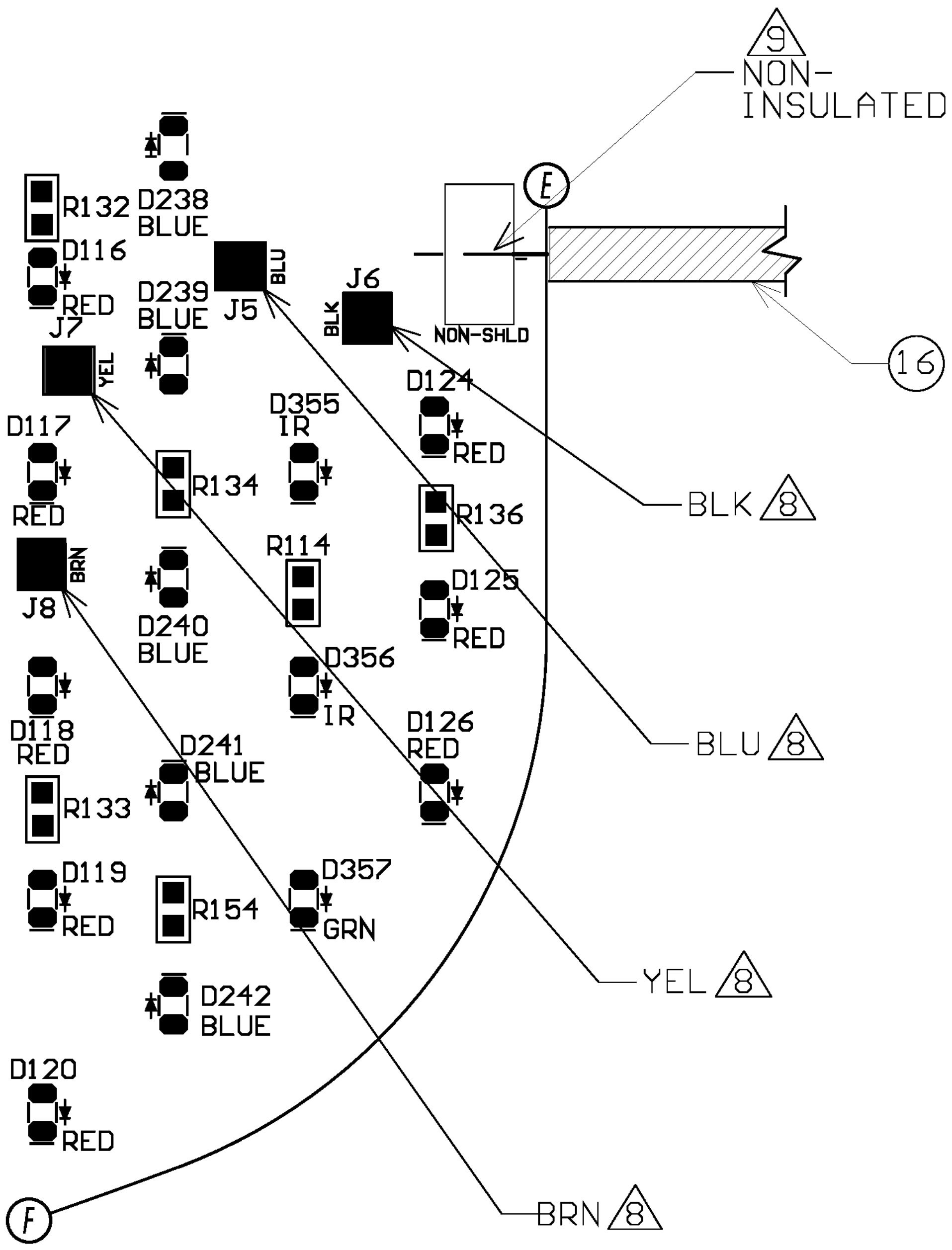
Figure 17:
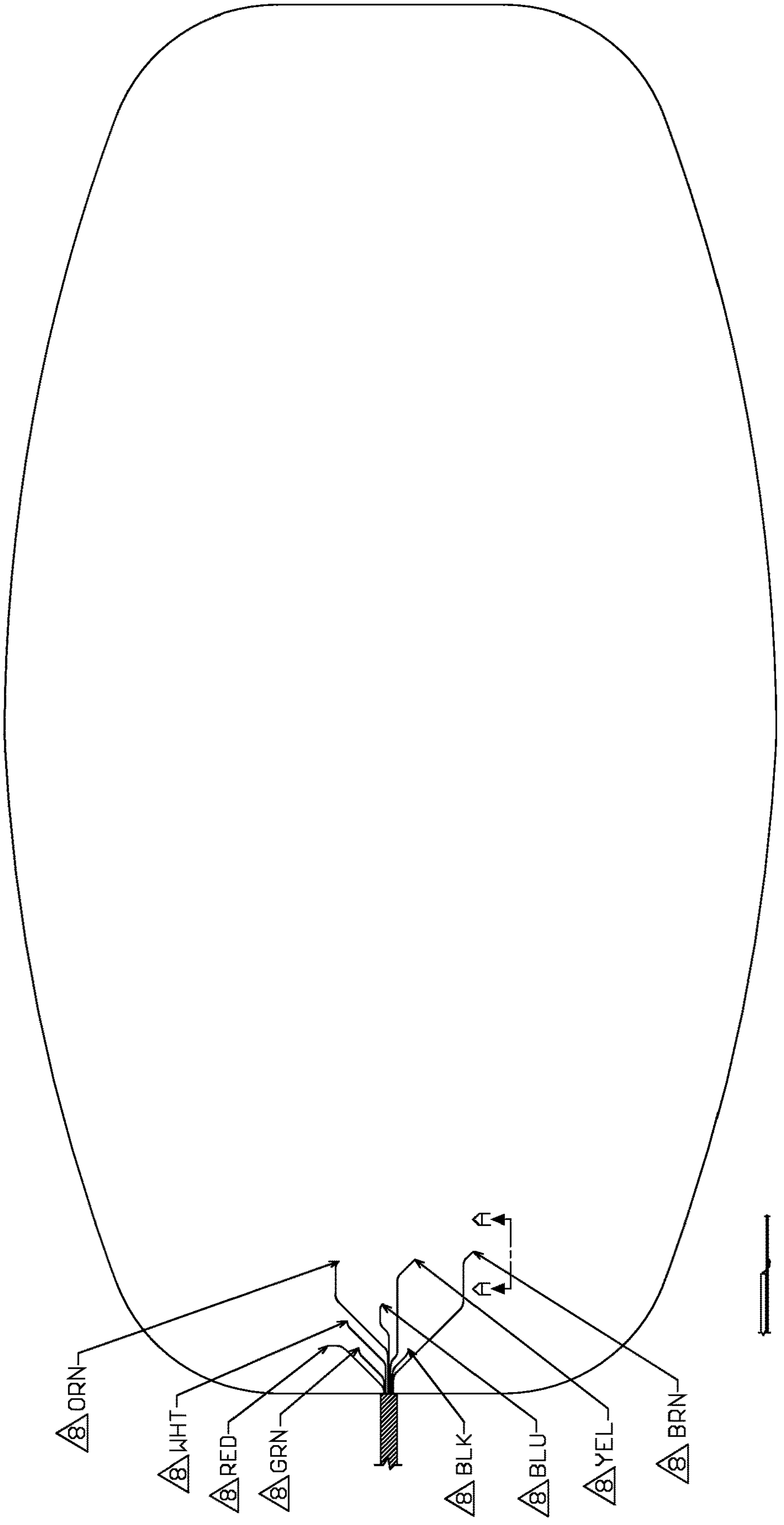
FIG. 17 is a secondary (rear) side view of a PCBA of an LED array useable in the shapeable light therapy device of FIG. 1
Figure 18:
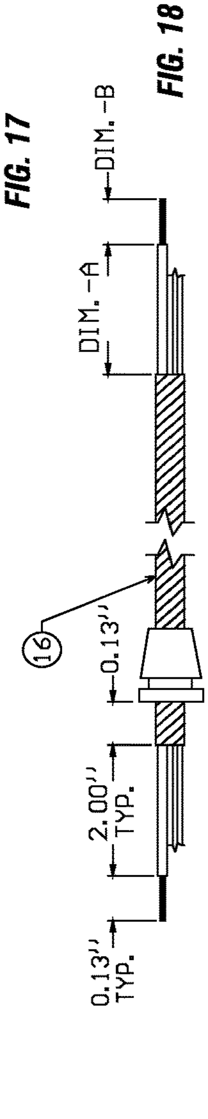
FIG. 18 is an enlarged sectional/assembly view of region A-A of FIG. 17.
Figure 19:
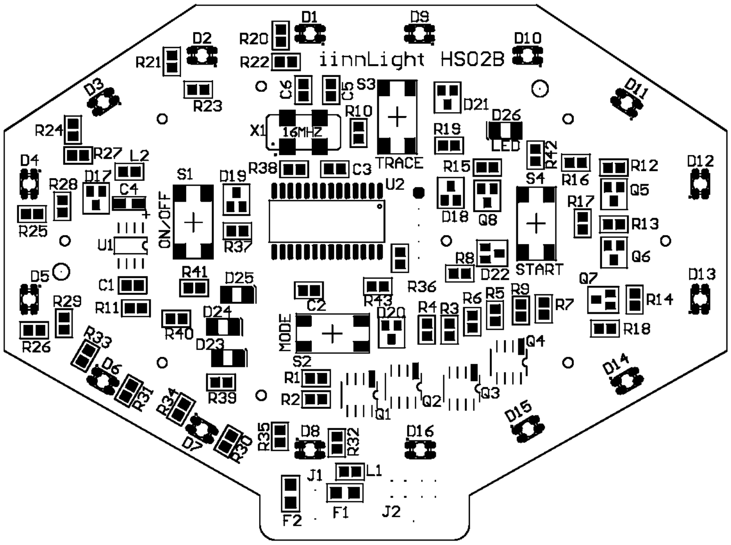
FIG. 19 is a primary (front) side view of a PCBA of a indicatoler circuit board usable in the system of FIG. 1.
Figure 20:
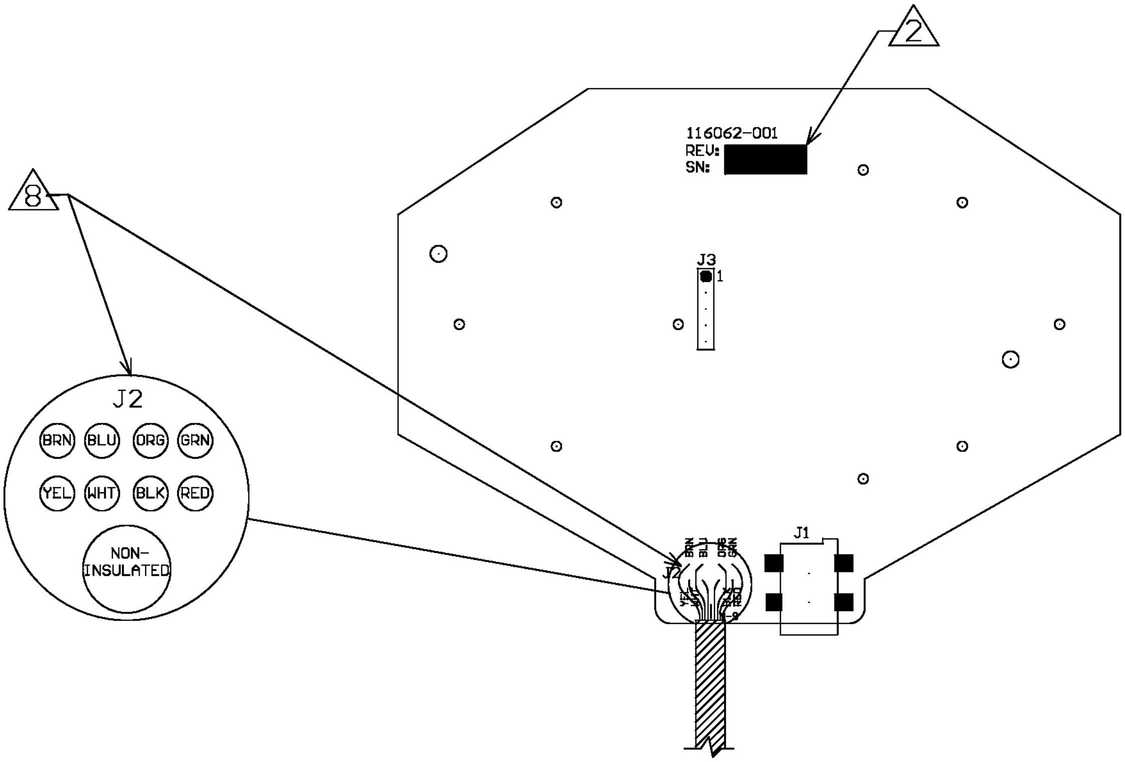
FIG. 20 is a secondary (rear) side view of a PCBA of a controller circuit board usable in the system of FIG. 1.

FIGS. 8 through 12 show several non-limiting examples of shapes that the shapeable pad light emitting apparatus 12 may be formed to and which the apparatus 12 will retain without the need for a strap or other retaining device. As illustrated in FIG. 12, the ability to place the apparatus 12 in various formed shapes allows it to be positioned so that it corresponds to (e.g., conforms to or tracks the shape of) the underlying area of the body to be treated (e.g., face, thigh, neck, etc.). Thus, for many common applications, the apparatus 12 may be hand-shaped to a configuration that allows it to be positioned over the body part to be treated with the therapeutic LEDs located as close as possible to the skin without the apparatus 12 actually touching the skin. Also, in some applications, this allows the ends of the apparatus 12 to be shaped so that the apparatus 12 may be stood upon an underlying surface (e.g., the surface of the bed or treatment table on which the subject is positioned) while the therapeutic LEDs are optimally positioned to deliver the desired phototherapy treatment.

In this example, the device 10 is programmed to deliver light therapy in a plurality of alternative light treatment modes intended for different therapeutic or cosmetic applications, including a) one light treatment mode wherein the emitted light is primarily infrared; b) another light treatment mode wherein the emitted light is primarily red; and c) yet another light treatment mode wherein the emitted light is primarily blue. Operation of the device 10 in the infrared treatment mode may cause the LEDs to emit light having a wavelength of, or of about, 880 nm. Operation of the device 10 in the red treatment mode may cause the LEDs to emit light having a wavelength of, or of about, 640 nm. Operation of the device 10 in the blue treatment mode may cause the LEDs to emit light having a wavelength of, or of about, 465 nm. As explained above, these different treatment modes may be selected depending on the pathological or cosmetic condition being treated and/or the depth of light penetration desired. See, Bartolet, D., *Light-Emitting Diodes* (*LEDs*) *in Dermatology*; Seminars in Cutaneous Medicine and Surgery, Vol. 27: pp. 227-238 (2008).

The user interface 14 may include a switch for turning the power on/off and a selector for selecting which treatment mode is desired. Also, optionally, the treatment times may be fixed or the user interface may include a timer set for setting the desired treatment time. Also, optionally, the device may be programmed to emit light in each treatment mode in either a pulsed (e.g., modulated) or non-pulsed fashion and the user interface may include a switch or function to allow the user to select or not select whether pulsing (e.g., modulation) is desired. For example, the device 10 may be sent to default to a pulsed delivery of light in each treatment mode unless the user inputs a signal through the user interface 14 to terminate the pulsing. More specifically, in this non-limiting example, when a light therapy session is initiated with the device set in the one treatment mode, the blue LEDs will emit blue light at a 1% duty cycle and the red and infrared LEDs will fade up from 1% to 90% in 20 seconds. When a light therapy session is initiated with the device set in another treatment mode, the blue LEDs will fade up from 1% to 90% in 20 seconds and the red and infrared LEDs will fade up from 1.3% to 2.5% in 2.5 seconds. Also, when a light therapy session is initiated with the device set in yet another treatment mode, the blue LEDs will fade up from 1% to 90% in 20 seconds and the red and infrared LEDs will cycle from 30% to 80% in 11.5 seconds. In this particular non-limiting example, each treatment mode will deliver pulsed light unless pulsation is turned off via the user interface 14, as follows: a) the first light treatment mode will deliver light at a pulse width modulation frequency of about 680 Hz unless pulse width modulation is turned off via the user interface 14; b) the second light treatment mode delivers light at a pulse width modulation frequency of about 800 Hz unless pulse width modulation is turned off via the user interface 14 and the third light treatment mode delivers light at a pulse width modulation frequency of about 80 Hz unless pulse width modulation is turned off via the user interface 14. As explained above, this ability to select the desired modulation (e.g., pulsation or non-pulsation) allowed the system 10 to be used to achieve different therapeutic effects. See, Bartolet, D., *Importance of Pulsing Illumination Parameters in Low-Level-Light Therapy*; Journal of Biomedical Optics, Vol. 15, No. 4: pp. 048001-048005 (2010).

In the particular example shown, the controller/user interface 14 includes indicator lights 15 for each of the available therapeutic modes for which the controller is programmed to perform (acne, anti-aging, aches & pains). When the on-off button 14*a* has been depressed to turn the system on, the controller initially defaults to a first mode (e.g., acne) and the indicator light for that mode begins to blink. If the user wishes to operate in that first mode, the user then presses the start button 14*b* which causes the first mode indicator light to stop blinking and remain on continually and also causes the therapeutic LEDs to begin the emit light in the selected first treatment mode. If the user wishes to operate in a treatment mode other than the first treatment mode, the user will push the treatment mode selector button 14*c* the appropriate number of times (i.e., once to shift to the second mode (anti-aging) and twice to shift the third mode (aches & pains), while the indicator light is still blinking. After the desired treatment mode is selected, the user will depress the start button and the system 10 will proceed to deliver therapy in the selected treatment mode, as will be indicated by non-blinking, constant illumination of the selected treatment mode indicator light.

Pressing the pulsation on/pulsation off button 14*d* will cause the light emitted by the therapeutic LEDs 23 to pulsate. Pressing the pulsation on/pulsation off button 14*d* again will cause the light emitted by the therapeutic LEDs 23 to be continuous (i.e., non-pulsating).

In some embodiments the controller/user interface 14 may include a display. Such display may display indications of whether the power is on or off and what light treatment mode has been selected. Optionally, such display may also display a treatment time that has been selected and/or elapsed and/or remaining; and, optionally, whether pulse width modulation is on or off.

It is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the substantial absence of other elements, steps, members, components, compositions, reactants, parts or portions unless otherwise noted. All reasonable additions, deletions, modifications and alterations are to be considered equivalents of the described examples and embodiments and are to be included within the scope of the following claims.

What is claimed is:

1. A light therapy device for delivering light therapy to a subject, said device comprising:

a flexible, light emitting pad that is formable into differing shapes, said pad comprising;

a deformable shape-retaining member which extends about a periphery of the pad and which has a central aperture, a flexible circuitry layer positioned in a central portion of the pad in axial alignment with the central aperture of the deformable shape retaining member, and a multiplicity of light emitters connected to the flexible circuitry layer, said light emitters being oriented to cast light from a light emitting side of the pad;

wherein, forming said pad from a flat configuration to a curved configuration causes the shape retaining member to deform and subsequently retain the pad in that curved configuration without need of a strap or other shape retaining member.

2. A device according to claim 1 further comprising a flexible translucent shield, barrier or panel which extends over the central portion of the pad on the light emitting side, thereby covering the light emitters.

3. A device according to claim 2 wherein the flexible translucent shield, barrier or panel comprises material that may be sanitized after use of the device.

4. A device according to claim 2 wherein the flexible shield, barrier or panel is configured such that, when the device is positioned with the flexible shield, barrier or panel in direct contact with a surface, adjacent light emitters will be within a therapeutically optimal distance of that surface.

5. A device according to claim 1 wherein said light emitters are operable to emit light in blue wavelengths, red wavelengths and infrared wavelengths.

6. A device according to claim 1 wherein the deformable shape-retaining member comprises a plastically deformable metal.

7. A device according to claim 1 wherein the shape-retaining member comprises a plastically deformable polymer.

8. A device according to claim 1 wherein the shape-retaining member comprises aluminum.

9. A device according to claim 1 wherein perforations are formed in end portions of the shape retaining member which reside in opposite ends of the pad.

10. A device according to claim 1 wherein the pad is formable to, and will retain, a configuration wherein a mid-region of the pad has an arched shape.

11. A device according to claim 10 which is positionable to deliver light therapy to a body part that is positioned on a table or other surface by placement of first and second end regions of the pad in contact with the table or other surface on opposite sides of the body part and the arcuate mid-region of the pad extends over the body part;

wherein the light emitting side of the pad is located on a bottom surface of the arcuate mid-region so that, when the pad is so positioned, light emitted from the light emitters will be cast on the body part.

12. A device according to claim 11 wherein the end regions of the pad are adjustable to raise or lower the light emitters relative to the body part.

13. A device according to claim 12 wherein the end regions are adjustable by deforming the end regions to differing configurations which result in raising or lowering the arcuate mid-region of the pad relative to the body part.

14. A device according to claim 13 wherein portions of the deformable shape retaining member that reside in the end regions of the pad have perforations formed therein to permit the end regions to be deformed to tighter curvatures than the mid-region.

15. A method for using a device according to claim 1 to deliver light therapy to a body part of a subject positioned on a table or other surface, said method comprising:

causing the pad to be formed into, and to retain, an arcuate shape;

positioning the pad, while in said arcuate shape, in an operative position wherein first and second end portions of the pad contact the table or other surface at locations on opposite sides of the body part and the arcuate pad extends over the body part such that light emitted from the light emitting side of the pad will be cast on the body part; and adjusting configurations of the first and second end portions to thereby adjust the distance between the light emitters and the body part.

16. A method according to claim 15 wherein the light emitters can emit at least red and blue light.

17. A method according to claim 15 wherein the light emitters are operable to simultaneously emit a plurality of wavelengths of light.

18. A method according to claim 17 wherein the light emitters are operable to simultaneously emit at least blue and red wavelengths of light.

19. A method according to claim 15 wherein the first and second end portions comprise feet configured to rest on the table or other surface.

20. A method according to claim 15 wherein the body part comprises a face of the subject.

21. A method according to claim 15 wherein the method is carried out for a purpose selected from: treatment of acne; reversal of signs of skin ageing; and relieving aches or pain.

* * * * *